(12) United States Patent
Nun

(10) Patent No.: US 6,328,747 B1
(45) Date of Patent: Dec. 11, 2001

(54) METHOD AND A SYSTEM FOR PERFORMING CATARACT SURGERY

(75) Inventor: Yehoshua Ben Nun, Doar Vitkin (IL)

(73) Assignee: ITOS Innovative Technology In Ocular Surgery, Ltd., Ra'Anana (IL)

( * ) Notice: Subject to any disclaimer, the term of this patent is extended or adjusted under 35 U.S.C. 154(b) by 0 days.

(21) Appl. No.: 09/156,982

(22) Filed: Sep. 18, 1998

Related U.S. Application Data

(63) Continuation-in-part of application No. 08/851,505, filed on May 8, 1997, now Pat. No. 6,217,584.

(30) Foreign Application Priority Data

| May 9, 1996 | (IL) | ......................................... 118208 |
| Dec. 1, 1996 | (IL) | ......................................... 119734 |

(51) Int. Cl.[7] ........................................ A61F 9/00
(52) U.S. Cl. ........................ 606/107; 606/180; 606/167; 604/22
(58) Field of Search .................... 606/107, 180, 606/167, 159; 604/19, 22

(56) References Cited

U.S. PATENT DOCUMENTS

| 3,732,858 | * | 5/1973 | Banko | ................................. 606/107 |
| 3,937,222 | * | 2/1976 | Banko | ................................. 606/107 |
| 3,976,077 | * | 8/1976 | Kerfoot | ................................. 606/107 |
| 4,061,146 | * | 12/1977 | Baehr et al. | ......................... 606/107 |
| 4,167,944 | * | 9/1979 | Banko | ................................. 606/107 |
| 4,168,707 | * | 9/1979 | Douvas et al. | ....................... 606/107 |
| 5,437,678 | * | 8/1995 | Sorensen | ............................. 606/107 |
| 5,690,641 | * | 11/1997 | Sorensen et al. | .................... 606/107 |

FOREIGN PATENT DOCUMENTS

| 099479 | 9/1990 | (IL) . |
| 103038 | 9/1992 | (IL) . |

* cited by examiner

Primary Examiner—Glenn K. Dawson
(74) Attorney, Agent, or Firm—Needle & Rosenberg, P.C.

(57) ABSTRACT

A cataract removing device (CRD) in a system for surgically removing a cataract from an eye includes a cryomanipulator having a body and a manipulator head with a cryogenic tip for selectively freeze-gripping a region of contact of the cataract and for manipulating it within the eye. The cryomanipulator may also include a surgical tip and a heating device. The cryomanipulator may further include a sleeve having an aperture associated with a supply of liquid for providing irrigation of the eye. The sleeve may be also associated with a vacuum suction device for producing suction at the aperture. The CRD is designed for breaking up the cataract while it is at least partially frozen by the cryomanipulator. The CRD includes a drilling unit for breaking the cataract and a handle for manipulating the drilling unit within the eye. The drilling unit includes a housing having a hollow member having an aperture therein for aspiring irrigation fluid from the eye and a drill bit rotatably disposed within the hollow member. The drill bit includes a drill shaft and a drill blade for breaking the cataract. The drill bit is rotatably couplable to a motor. The housing may also include a second hollow member surrounding the first hollow member for providing irrigation fluid to the eye and for aspiring excess irrigation fluid and fragments of the broken cataract. The housing may also include a guard lip. The drilling unit may be disposable.

28 Claims, 18 Drawing Sheets

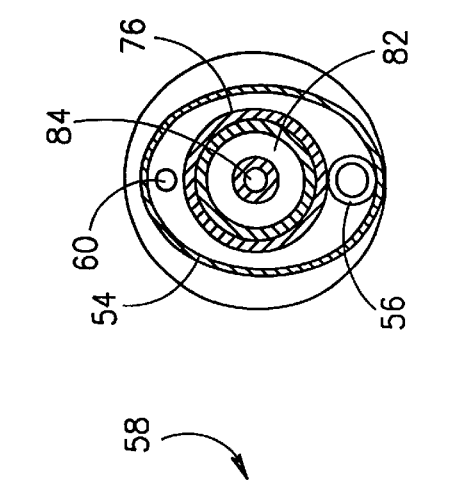
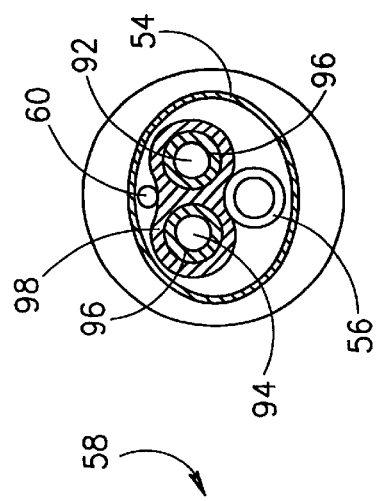
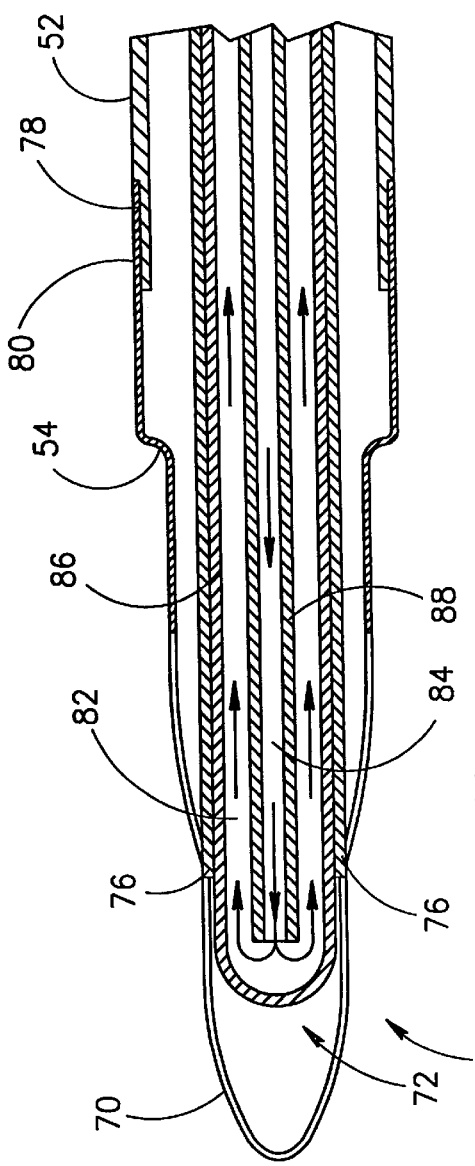
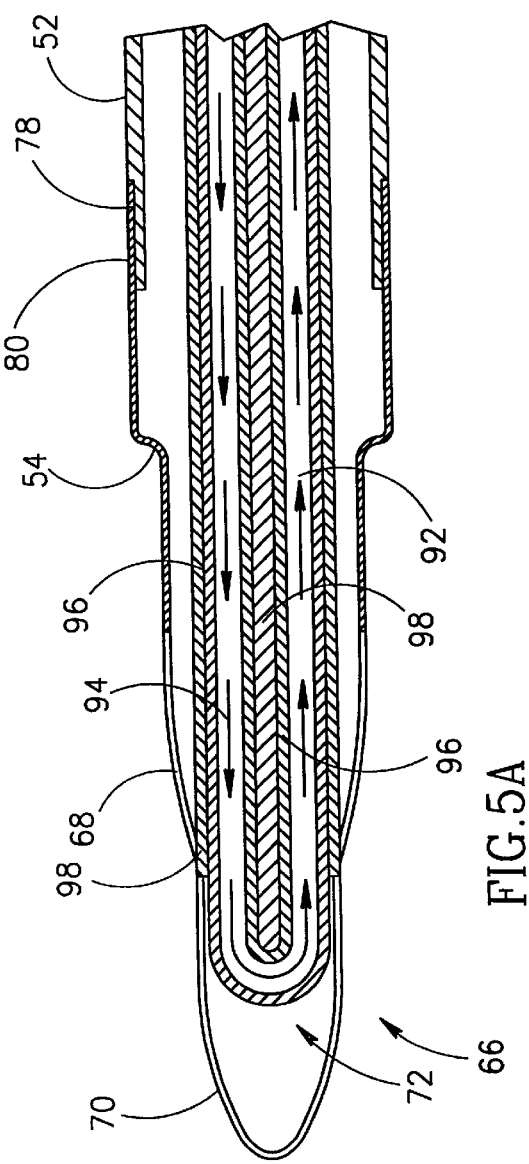

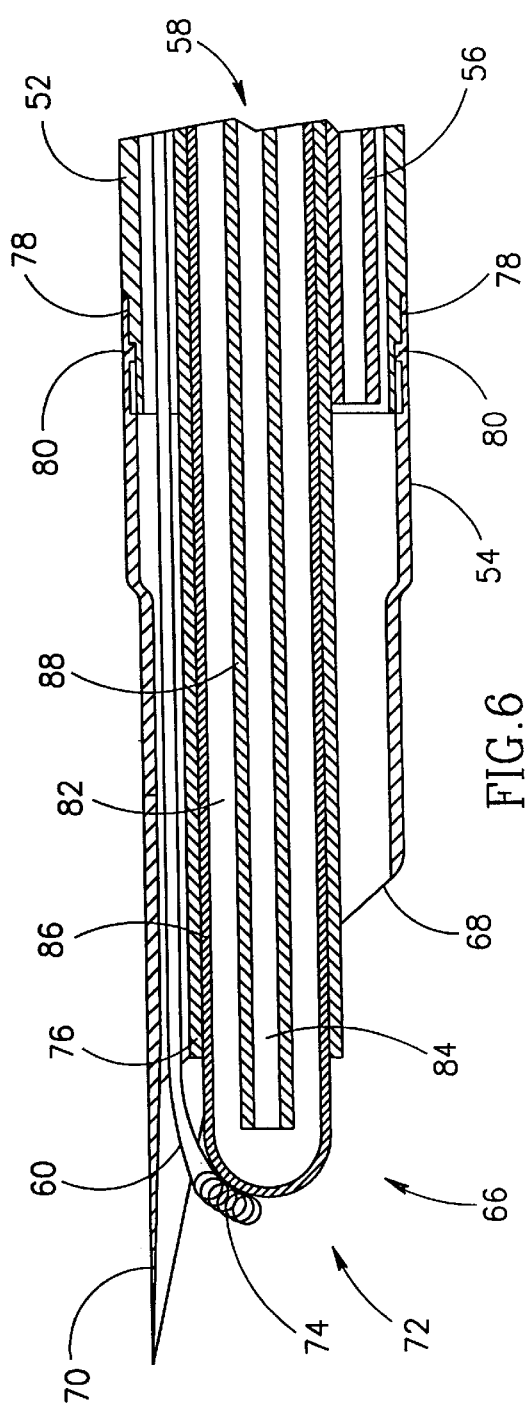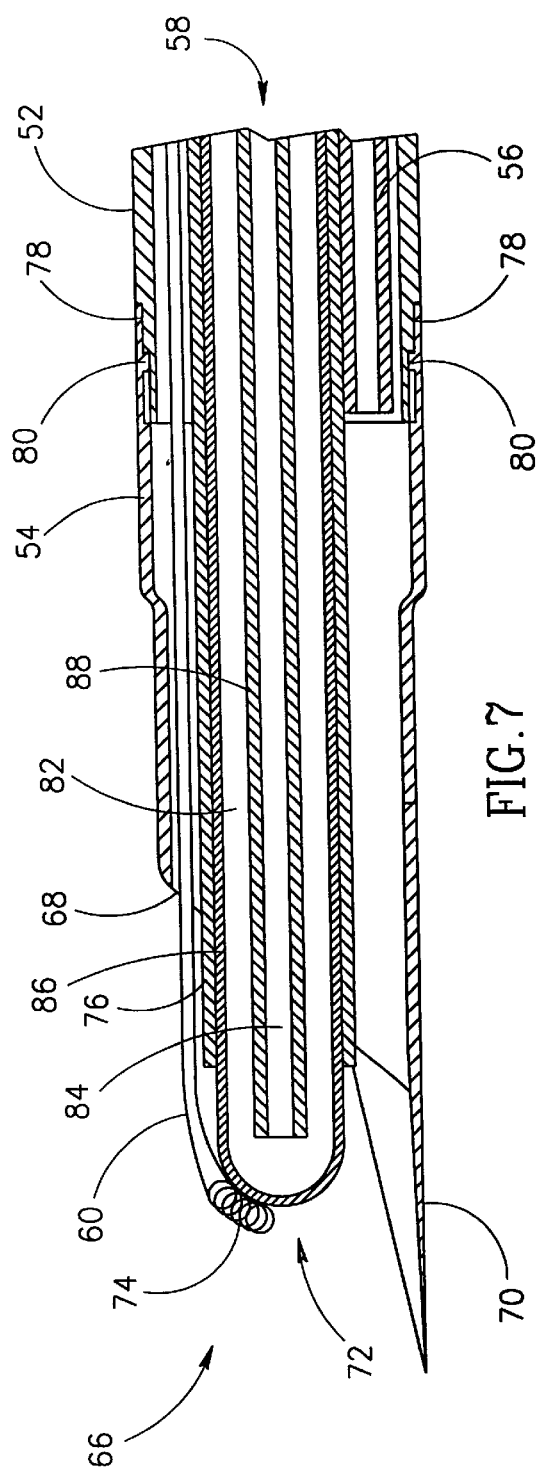

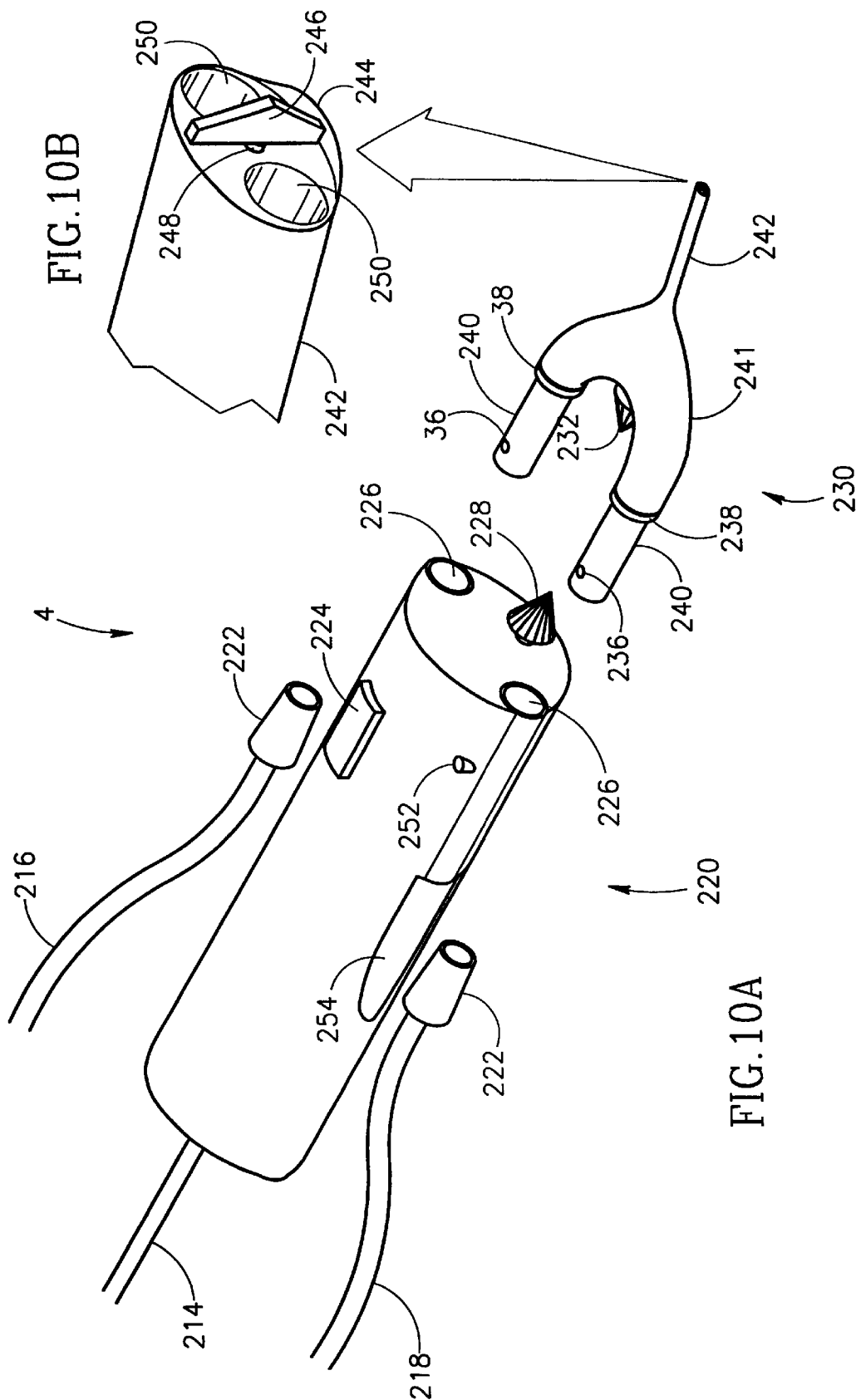

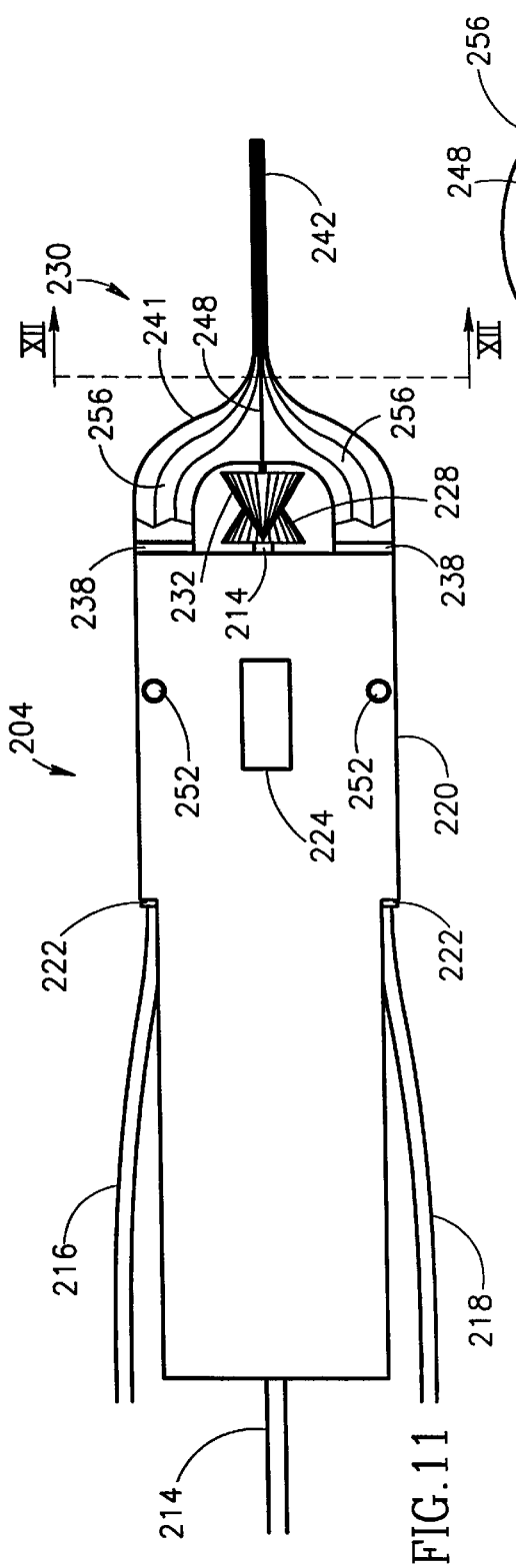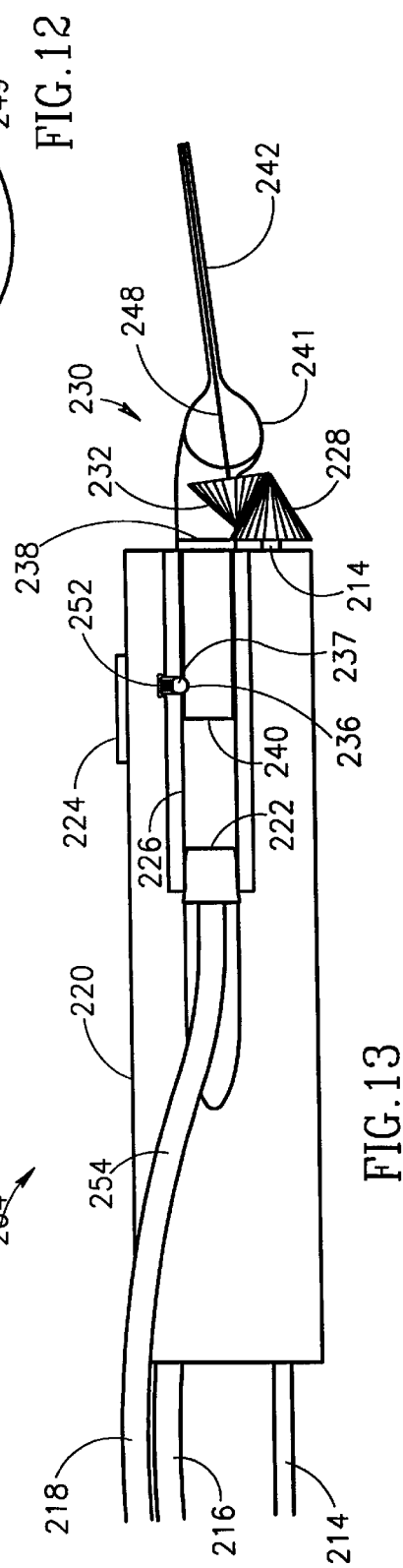

METHOD AND A SYSTEM FOR PERFORMING CATARACT SURGERY

RELATION TO OTHER APPLICATIONS

This application is a continuation in part of U.S. patent application Ser. No. 08/851,505 filed May 8, 1997 and entitled "A METHOD AND SYSTEM FOR PERFORMING CATARACT SURGERY", now U.S. Pat. No. 6,217,584.

FIELD OF THE INVENTION

The present invention relates to the field of devices for eye surgery in general and to the field of devices for cataract surgery in particular.

BACKGROUND OF THE INVENTION

Surgical removal of cataract is well known in the art. In cataract surgery, the content of the eye lens is completely removed leaving only the posterior lens capsule, in which an artificial lens may be subsequently installed. It is appreciated that one of the main risks in cataract surgery is a potential damage, e.g. rupture, of the lens capsule. In the past, it was common practice to "freeze" the entire lens using appropriate means and then, to remove the lens in its entirety via a large opening which is formed in the cornea, specifically, along the Cornea Limbus. This procedure resulted in damage to the lens capsule and to the vitreous body and is, therefore, no longer in use.

Presently, there are a number of known methods for removing cataract. FIG. 1 schematically illustrates a cross-sectional view of a human eye 10 during cataract surgery in accordance with one, commonly used, prior art method. A surgical instrument 12 and, optionally, a manipulation device 14, are inserted into eye lens 20 via cornea 16, a preferably dilated pupil 18 and an opening formed in the anterior capsule of lens 20. As is known in the art, lens 20 includes a core 28, known as the nucleus, which is formed of a relatively hard tissue. Core 28 is surrounded by a layer 26 of relatively soft, jell-like tissue, known as the cortex, which fills lens capsule 24.

The soft tissue in cortex layer 26 is typically removed gradually using a vacuum suction device and/or a "scooping" device (not shown in the drawings). To remove nucleus 28, the hard tissue is typically, first, broken into small fragments and/or dissolved using appropriate instruments and/or solutions and, then, removed gradually by suction and/or "scooping" as described above. Alternatively, the entire nucleus can be removed in one piece, however, this requires cutting a large opening in the cornea.

FIG. 1 illustrates one method of breaking nucleus 28 using directional ultrasonic transmission. According to this method, instrument 12 includes a device 25, generally known as a Phacoemulsifier (Hereinafter: "Phaco"), which transmits intense ultrasonic energy into nucleus 28. The crushing effect of the ultrasonic transmission of Phaco device 25 is typically enhanced by a stream of liquid 22 supplied from an external sleeve 23 of instrument 12, which liquid typically includes a dissolving agent. It is appreciated that, during surgery, a constant supply of liquids is generally required to compensate for escape of intraocular liquids and/or to assist in dissolving the content of lens 20. In the example shown in FIG. 1, the supply of liquid 22 via sleeve 3 is utilized both as a dissolving agent and as a compensatory liquid supply. However, it is appreciated that a separate liquid supply may additionally or alternatively be used.

Manipulation device 14 typically includes a thin, pointed instrument. For example, The thin pointed instrument can be a needle or a spatula, which provide partial counter-support to the operation of instrument 12 on nucleus 28. Such a device enables the surgeon to manipulate nucleus 28 by pushing it to a desired position and to temporarily support the nucleus at the desired position. However, it should be noted that the ability of the surgeon to manipulate and control nucleus 28 using device 14 is limited, due to various physical parameters. For example, the "angle of the attack" of device 14 on the traction between device 14 and the surface of nucleus 28 can be manipulated, using device 14, only by pushing and not by pulling.

Medical follow up studies reveal that the quality of the post-operative optical results depends on the size of the incision made during surgery, where smaller incisions are usually associated with better post-operative results.

An additional development favoring the reduction of the incision size is the availability of foldable artificial lenses which can be introduced into the eye and inserted into the capsula while folded inside a needle-like device of relatively small diameter.

Unfortunately, ultrasonic systems such as the Phacoemulsifier are relatively expensive. Moreover, during the operation, the surgeon cannot observe a clearly defined border of the crushing action of the Phaco device 25. Thus, the inexperienced surgeon might inadvertently damage the posterior capsule of the lens, resulting in poorer post-operative results.

Additionally, the geometry of the crushing zone around the tip of the Phaco device 25 is not constant and varies for different sonication intensities, while having no visible cue which the surgeon can use to determine the precise crushing range from the tip of the Phaco device 25.

Consequently, there is a steep learning curve for the surgeon, requiring a relatively long training period and resulting in lower quality of the post-operative results during the training period.

Furthermore, in certain cataract cases, the degree of hardening of the cataract nucleus 28 is such that the Phaco device 25 cannot crush it, thus, requiring the surgeon to broaden the small incision in order to remove the whole cataract nucleus.

SUMMARY OF THE INVENTION

The present invention seeks to provide an improved device for manipulating tissue during surgery. The manipulation device of the present invention is particularly useful in intraocular surgery, particularly in cataract removal surgery.

The present invention provides a device, hereinafter referred to as cryomanipulator, having a selectively activated cryogenic tip designed to be inserted into a surgical site, e.g., into an eye lens, and to contact a tissue to be manipulated, for example the nucleus of an eye lens. In response to the selective activation thereof, the cryogenic tip selectively adheres to a portion of the tissue, die to the freezing of the tissue adjacent the tip. This adherence of the cryogenic tip to the manipulated tissue, at the region of contact therebetween, will be hereinafter referred to as a "freeze-grip". As long as the cryogenic tip is active, i.e., as long as the freeze-grip is active, the tissue can be securely and conveniently manipulated in any direction, e.g., pushed pulled, twisted, etc., by appropriate movement of the cryomanipulator. When the cryogenic tip is deactivated, the freeze-grip is released and the tip can be moved to a new position or location vis-a-vis the tissue. Thus, by sequentially positioning, activating, deactivating, repositioning the cryomanipulator, the tissue can be manipulated efficiently, quickly and accurately during surgery.

The cryomanipulator is preferably used in conjunction with a surgical instrument, for example a Phacoemulsifier device or any other means for crushing hard tissue, which operates on the tissue while the tissue is temporarily supported by the cryomanipulator. It should be noted that the freeze-grip between the cryogenic tip and the tissue provides a firm, stable support to the manipulated tissue, allowing convenient operation of the surgical instrument.

In a preferred embodiment of the present invention, the cryomanipulator includes a supply of liquid, preferably an intraocular-compatible liquid, adjacent to or juxtaposed with the cryogenic tip. The supply of liquid expedites the release of the freeze-grip when the cryogenic tip is deactivated, allowing quicker repositioning of the cryomanipulator and, thus, improving the efficiency and accuracy of the cryomanipulator.

In some preferred embodiments of the present invention, the cryomanipulator includes a heating device juxtaposed with the cryogenic tip. The heating device is preferably activated with the cryogenic tip. The heat provided by the heating device maintains a biocompatible temperature along the cryomanipulator's shaft and expedites the release of the freeze-grip, improving the manipulation efficiency of the cryomanipulator and avoiding damage to the intra-ocular structures adjacent to the shaft backwards of the tip.

In some preferred embodiments of the present invention, the cryomanipulator includes an open sleeve which surrounds the cryogenic tip and the heating device, if used. Preferably, the sleeve includes a removable sleeve. In one preferred embodiment of the present invention, the sleeve is associated with a source of a predetermined liquid, providing the liquid supply described above. Alternatively, the sleeve may be associated with a vacuum suction device, enabling suction of tissue removed during surgery. Preferably, the sleeve is associated with a flow selector, as is known in the art, which enables switching of the cryomanipulator between a number of modes of operation, e.g., a liquid supply mode and a vacuum suction mode.

In some preferred embodiments of the present invention, the cryomanipulator includes a surgical tip, for example a blade juxtaposed with the cryogenic tip to a desired position on the tissue. In the preferred embodiments using a removable sleeve, the surgical instrument preferably mounted on the removable sleeve.

There is thus provided, in accordance with a preferred embodiment of the present invention, a device for manipulating tissue during surgery including a manipulator head having a cryogenic tip adapted to engage a region-of-contact of the tissue and to selectively freeze-grip the region of contact.

In a preferred embodiment of the present invention, the device further includes a sleeve surrounding the cryogenic tip and having an aperture directed generally towards the region-of-contact. Preferably, the sleeve is associated with a supply of liquid which is expelled through the aperture. Additionally or alternatively, the sleeve is associated with a vacuum suction device which produces suction at the aperture. Preferably, the device has a body and the sleeve is removably mounted on the body.

In a preferred embodiment of the invention, the sleeve includes a surgical tip juxtaposed with the cryogenic tip.

In a preferred embodiment of the present invention, the manipulator head includes a heating device juxtaposed with the cryogenic tip. Preferably, the device includes means for selectively activating the heating device to heat a vicinity of the region-of-contact.

Further, in accordance with a preferred embodiment of the present invention, there is provided a device for manipulating tissue during surgery including:

a manipulator head having a cryogenic tip adapted to engage a region-of-contact of the tissue; and means for selectively activating the cryogenic tip to freeze-grip the region of contact.

In some preferred embodiments of the present invention, the device further includes means for supplying liquid generally towards the region-of-contact. Additionally or alternatively, the device includes means for heating a vicinity of the region-of-contact and for thermal control of the shaft backwards to the region of contact.

In a preferred embodiment of the present invention, the manipulatory head includes a surgical tip juxtaposed the cryogenic tip. Preferably, the surgical tip includes a blade.

In a preferred embodiment of the present invention, the tissue includes an intraocular tissue. Preferably, the intraocular tissue includes a portion of an eye lens. More preferably, the tissue includes at least a portion of the nucleus of the eye lens.

The present invention also seeks to provide a device for the breaking (disintegrating) and removing of a cataract which can be inserted into the eye through a relatively small incision.

The present invention further seeks to provide a device for breaking and removing a cataract in which the part that comes in contact with the patient's eye is a disposable part.

There is therefore provided, in accordance with a preferred embodiment of the present invention, a device for removing a cataract from an eye while at least a part the cataract is being held by a freeze-grip and is in a solid like state. The device includes a drilling unit for breaking the cataract, and a handle connectable to the drilling unit for enabling an operator to manipulate the drilling unit within the eye.

Further, in accordance with a preferred embodiment of the present invention, the drilling unit includes a housing having a bore therewithin and a drill bit rotatably disposed within the bore, and couplable to an external motor.

Yet further, in accordance with another preferred embodiment of the present invention, the handle of the device also includes a motor and the drilling unit includes a housing having a bore therewithin and a drill bit rotatably disposed within the bore, wherein the drill bit is couplable to the motor.

Still further, in accordance with yet another preferred embodiment of the present invention, the drilling unit further includes a conduit, connectable to an irrigation fluid reservoir, for providing irrigation fluid to the anterior chamber of the eye.

Additionally, in accordance with another preferred embodiment of the present invention, the drilling unit further includes a second conduit connectable to a vacuum pump for aspiring excessive irrigation fluid and fragments of the cataract suspended in the irrigation fluid from the anterior chamber of the eye.

There is therefore also provided, in accordance with another preferred embodiment of the present invention, a drilling unit for removing a cataract from an eye, while at least part of the cataract is freeze-gripped in a solid like state. The drilling unit includes a housing having a bore therewithin, a drill bit rotatably disposed within the bore and a conduit for providing irrigation fluid to the anterior chamber of the eye. The drill bit is rotatably couplable to a motor and the conduit is connectable to an irrigation fluid reservoir.

Further, in accordance with another preferred embodiment of the present invention, the drilling unit further includes a second conduit connectable to a vacuum pump for aspiring excessive irrigation fluid and fragments of the cataract suspended in the irrigation fluid from the anterior chamber of the eye.

There is therefore also provided, in accordance with another preferred embodiment of the present invention, a system for removing a cataract from an eye, while the cataract is in a solid-like state. The system includes a drilling unit for breaking the cataract, a handle attachable to the drilling unit for enabling an operator to manipulate the drilling unit within an eye and a motor for powering the drilling unit.

further, in accordance with another preferred embodiment of the present invention, the system also includes a reservoir of irrigation fluid for supplying irrigation fluid to the drilling unit.

still further, in accordance with yet another preferred embodiment of the present invention, the drilling unit includes a housing having a bore therewithin, a drill bit rotatably disposed within the bore and a conduit for providing irrigation fluid to the anterior chamber of the eye. The conduit is connectable to the reservoir of irrigation fluid and the drill bit is couplable to the motor.

Additionally, in accordance with another preferred embodiment of the present invention, the system also includes a vacuum pump for aspiring excessive irrigation fluid and fragments of the cataract suspended in the irrigation fluid from the anterior chamber of the eye.

Yet further, in accordance with another preferred embodiment of the present invention, the drilling unit further includes a second conduit connectable to the vacuum pump for aspiring excessive irrigation fluid and fragments of the cataract suspended in the irrigation fluid from the anterior chamber of the eye.

According to yet another preferred embodiment of the present invention, the system also includes at least one controlling unit for controlling the vacuum pump and the motor, for regulating the rate of suction of the vacuum pump and the speed of rotation of the motor.

Furthermore, in accordance with still another preferred embodiment of the present invention, the drilling unit of the system is a disposable unit.

Further, in accordance with another preferred embodiment of the present invention, the drill bit includes a drill blade and the housing of the drilling unit also includes a guard lip protruding from an end of the housing proximal to the drill blade.

There is therefore also provided, in accordance with another preferred embodiment of the present invention, a system for removing a cataract from an eye, while the cataract is in a solid-like state. The system includes a drilling unit for breaking the cataract, a handle attachable to the drilling unit for enabling an operator to manipulate the drilling unit within an eye and a motor for powering the drilling unit.

Further, in accordance with another preferred embodiment of the present invention, the system also includes a reservoir of irrigation fluid for supplying irrigation fluid to the drilling unit.

Still further, in accordance with yet another preferred embodiment of the present invention, the drilling unit includes a housing having a bore therewithin, a drill bit rotatably disposed within the bore and a conduit for providing irrigation fluid to the anterior chamber of the eye. The conduit is connectable to the reservoir of irrigation fluid and the drill bit is couplable to the motor.

Additionally, in accordance with another preferred embodiment of the present invention, the system also includes a vacuum pump for aspiring excessive irrigation fluid and fragments of the cataract suspended in the irrigation fluid from the anterior chamber of the eye.

Yet further, in accordance with another preferred embodiment of the present invention, the drilling unit further includes a second conduit connectable to the vacuum pump for aspiring excessive irrigation fluid and fragments of the cataract suspended in the irrigation fluid from the anterior chamber of the eye.

According to yet another preferred embodiment of the present invention, the system also includes at least one controlling unit for controlling the vacuum pump and the motor, for regulating the rate of suction of the vacuum pump and the speed of rotation of the motor.

Furthermore, in accordance with still another preferred embodiment of the present invention, the drilling unit of the system is a disposable unit.

Further, in accordance with another preferred embodiment of the present invention, the drill bit includes a drill blade and the housing of the drilling unit also includes a guard lip protruding from an end of the housing proximal to the drill blade.

There is therefore also provided, in accordance with still another preferred embodiment of the present invention, a method for removing a cataract from an eye. The method includes the steps of solidifying the cataract and the step of breaking the cataract while it is solidified.

Further, in accordance with yet another preferred embodiment of the present invention, the method also includes the steps of irrigating the anterior chamber of the eye with an irrigation fluid and removing excessive irrigation fluid and fragments of the cataract suspended in the irrigation fluid from the anterior chamber of the eye by aspiration.

Furthermore, in accordance with still another preferred embodiment of the present invention, the step of solidifying includes the step of freezing the cataract.

Still Further, in accordance with yet another preferred embodiment of the present invention, the step of solidifying includes the step of freezing the cataract by a cryomanipulator.

Further, in accordance with yet another preferred embodiment of the present invention, the step of breaking is performed by a cataract removing device.

Furthermore, in accordance with still another preferred embodiment of the present invention, the step of breaking includes the step of immobilizing the cataract by freeze-gripping it with the cryomanipulator prior to breaking the cataract.

Furthermore, in accordance with still another preferred embodiment of the present invention, the step of irrigating and the step of removing are performed by the cataract removing device.

Furthermore, in accordance with still another preferred embodiment of the present invention, the cataract removing device includes a drilling unit for breaking the cataract and a handle connectable to the drilling unit for manually manipulating the drilling unit within the eye.

There is further provided, in accordance with still another preferred embodiment of the present invention, a method for removing a cataract from an eye. The method includes the steps of inserting a cryomanipulator and a surgical instrument through the eye to contact the cataract, immobilizing at least part of the cataract by freeze-gripping it with the cryomanipulator, breaking the cataract into fragments using the surgical instrument and removing the fragments from the eye.

Furthermore, in accordance with still another preferred embodiment of the present invention, the surgical instrument is a cataract removing device, the cataract removing device includes a drilling unit for breaking the cataract and a handle connectable to the drilling unit for manually manipulating the drilling unit within the eye and wherein the step of immobilizing further includes the step of solidifying at least part of the cataract by freezing at least part of the cataract with the cryomanipulator, and the step of breaking includes breaking the cataract by the drilling unit while at least part of the cataract is immobilized and at least partially frozen by the cryomanipulator.

Furthermore, in accordance with still another preferred embodiment of the present invention, the step of inserting includes the steps of forming two suitable tracts in the eye, the tracts extending from the sclero-corneal region of the eye through the anterior chamber of the eye to the cataract, introducing the cryomanipulator and the surgical instrument into the eye through the tracts and forming at least one opening in the anterior capsule of the eye for inserting the cryomanipulator and the surgical instrument into the cataract.

Furthermore, in accordance with still another preferred embodiment of the present invention, the surgical instrument is a cataract removing device and the step of removing includes aspirating the fragments of the cataract by at least one of the cryomanipulator and the cataract removing device.

Furthermore, in accordance with still another preferred embodiment of the present invention, The step of breaking further includes immobilizing at least one of the fragments of the cataract by freeze-gripping it with the cryomanipulator.

Furthermore, in accordance with still another preferred embodiment of the present invention, The method further includes the step of manipulating at least part of the cataract within the lens capsule while it is freeze-gripped by the cryomanipulator for facilitating the breaking of the part by the cataract removing device.

Furthermore, in accordance with still another preferred embodiment of the present invention, The method further includes the step of manipulating at least part of the cataract within the lens capsule while it is freeze-gripped by the cryomanipulator for facilitating the breaking of the part by the surgical instrument.

Finally, in accordance with still another preferred embodiment of the present invention, The step of irrigating and the step of removing are performed by the cryomanipulator.

BRIEF DESCRIPTION OF THE DRAWINGS

The invention is herein described, by way of example only, with reference to the accompanying drawings, wherein:

FIGS. 4A and 4B are, respectively, top view and front view, cross-sectional, schematic illustrations of one preferred variation of a cryomanipulator of FIG. 2;

FIGS. 5A and 5B are, respectively, top view and front view, cross-sectional, schematic illustrations of another preferred variation of the cryomanipulator of FIG. 2;

FIGS. 6 and 7 are schematic, side view, illustrations of two, respective, preferred mounting configurations of a removable sleeve of the cryomanipulator of FIG. 2;

FIG. 10A is a schematic isometric view illustrating the cataract removing device (CRD) of the cataract removing system of FIG. 9;

FIG. 10B is a, schematic, isometric view illustrating in detail the tip of the disposable drilling unit which is part of the cataract removing device (CRD) of FIG. 10A;

FIG. 11 is a schematic top view of the CRD of FIG. 10A illustrating the disposable drilling unit assembled with the handle of the CRD;

FIG. 12 is a schematic cross section of the disposable drilling unit of FIG. 11 along the line XII—XII;

FIG. 13 is a schematic side view of the CRD of FIG. 11 illustrating the disposable drilling unit assembled with the handle of the CRD;

DETAILED DESCRIPTION OF THE INVENTION

Figure 1:
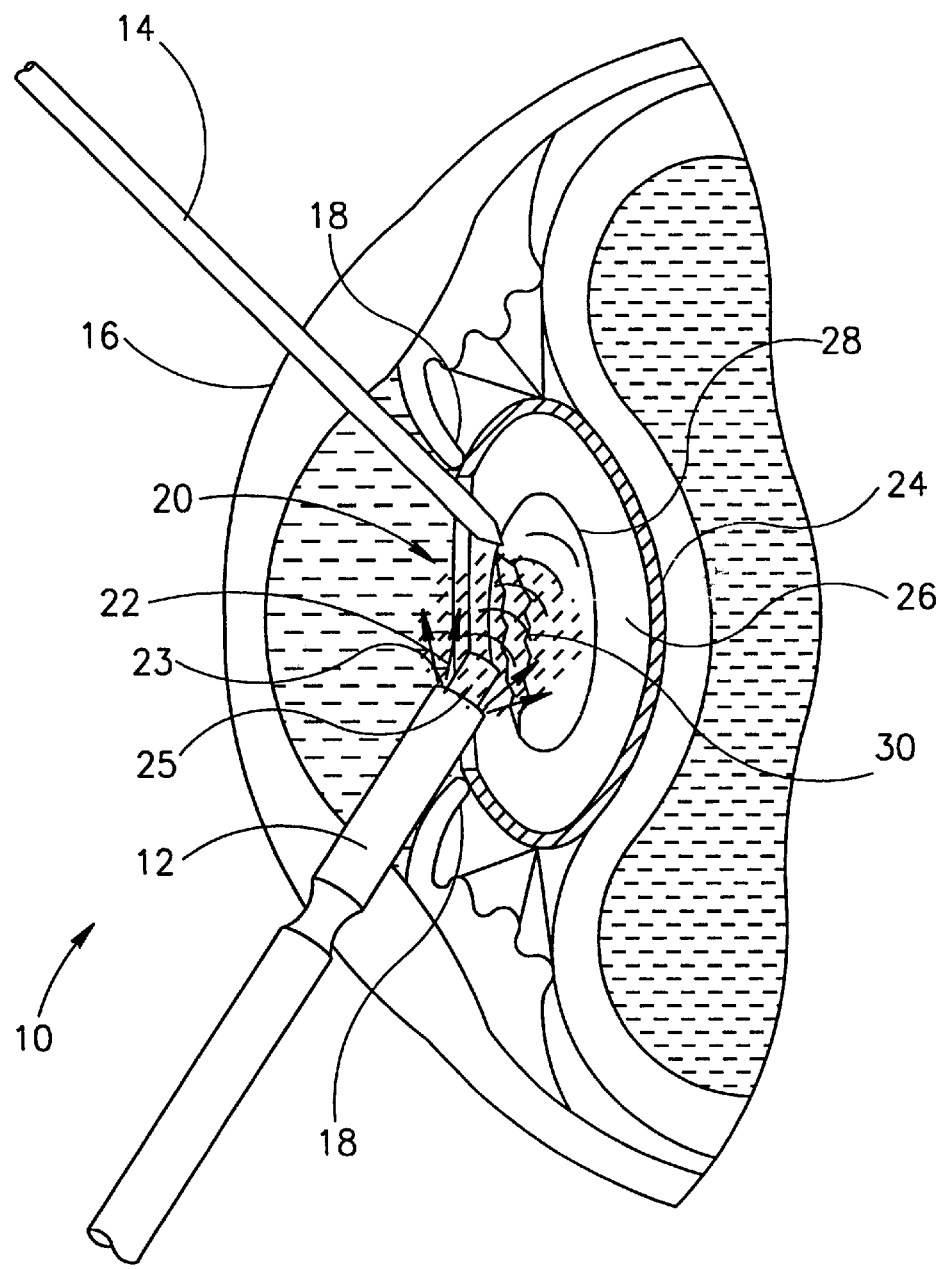
FIG. 1 is a schematic, side view, cross-sectional illustration of a human eye during cataract surgery in accordance with the prior art.

It is noted that, for a better understanding, like components are designated by like reference numerals throughout the various figures.

Figure 2:
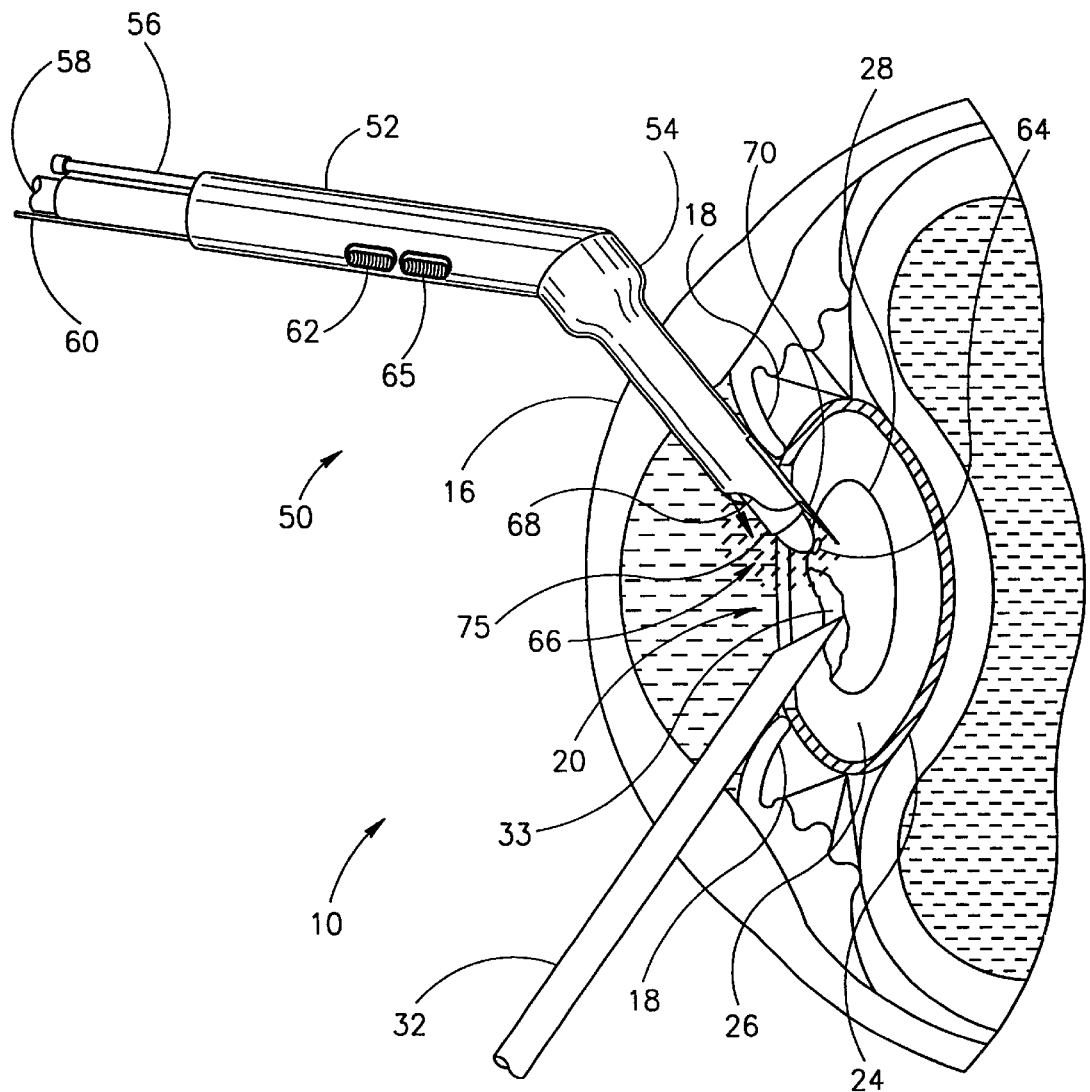
FIG. 2 is a schematic, side view, cross-sectional illustration of a human eye during cataract surgery using a cryomanipulator in accordance with a preferred embodiment of the present invention.

Reference is now made to FIG. 2, which schematically illustrates a cross-sectional side view of human eye 10 during cataract surgery in accordance with a preferred embodiment of the present invention. A cryomanipulator 50, described in detail below, and a surgical instrument 32 are inserted into eye lens 20 via cornea 16 and dilated pupil 18. As is known in the art, lens 20 consists of lens capsule 24, soft cortex layer 26 and hard nucleus 28, as described above with reference to FIG. 1. Surgical instrument 32 may include any surgical instrument known in the art, for example a blade and/or an ultrasonic transmitter such as a Phacoemulsifier (hereinafter: "Phaco") and/or a "scooping" device. In a preferred embodiment of the present invention, cryomanipulator 50 includes a manipulator head 66 adapted to engage nucleus 28 of lens 20, at a region of contact 64, while surgical instrument 32 operates on a region 33 of nucleus 28. Additionally or alternatively, cryomanipulator 50 may be utilized as a surgical instrument, e.g., for removing tissue from layer 26 and/or for removing tissue separated from region 33, as explained below.

Figure 3:
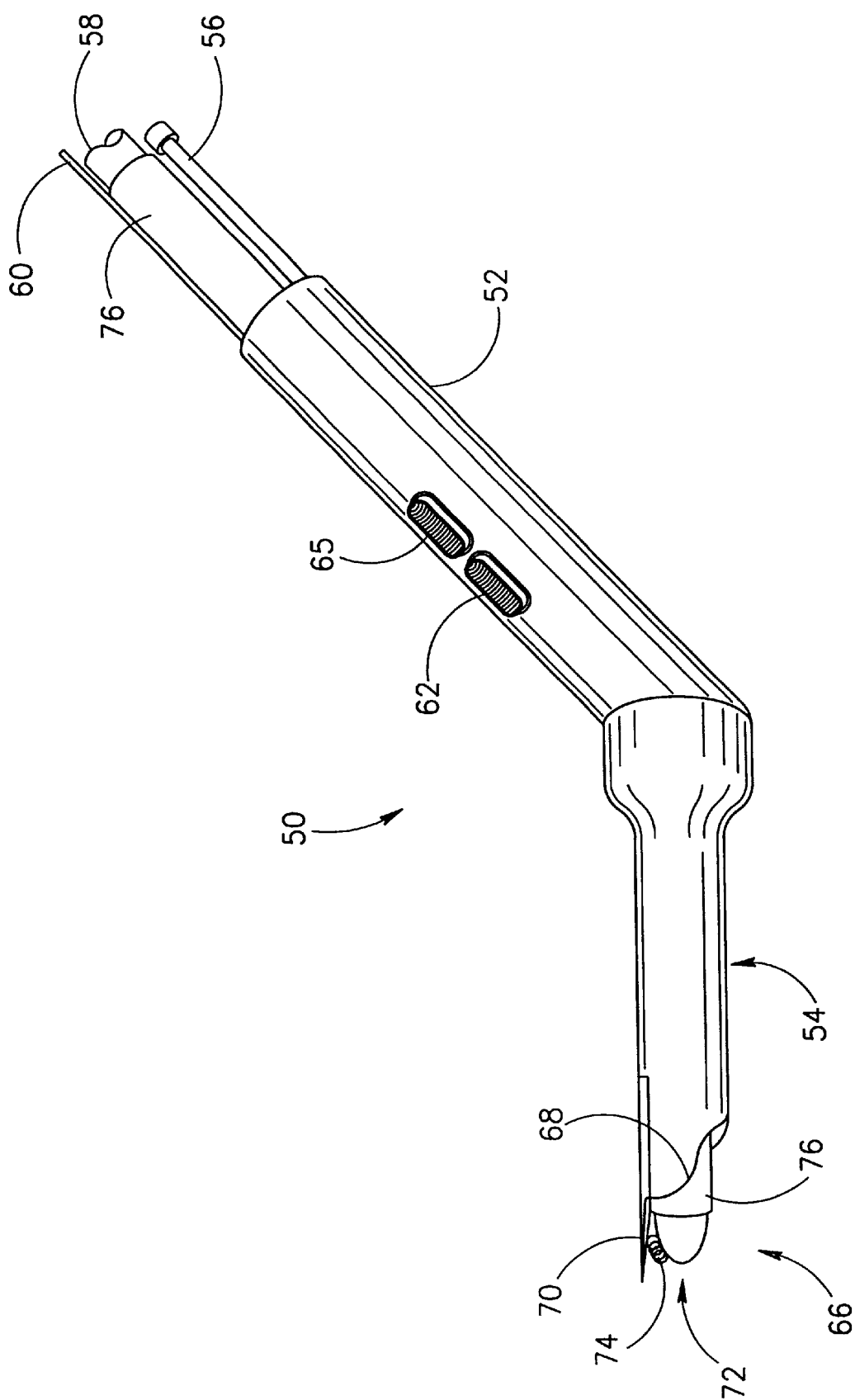
FIG. 3 is a schematic, enlarged, side view illustration of the cryomanipulator of FIG. 2.

Reference is now made also to FIG. 3 which schematically illustrates an enlarged side-view of cryomanipulator 50. The cryomanipulator 50 preferably includes a body portion 52 and a sleeve portion 54, preferably a removable sleeve as described in detail below. In accordance with the present invention, manipulator head 66 includes a selectively-activated cryogenic tip 72 adapted to be in contact with region 64 of nucleus 28. Tip 72 is preferably selectively activated by a surgeon using a switch 62 on body portion 52, as described below. When cryogenic tip 72 is activated, the tissue in region 64 freezes and, thereby, adheres to the cryogenic tip. This adherence of tip 72 to region 64 will be hereinafter referred to as a "freeze-grip".

As long as tip 72 is active, the freeze grip enables the surgeon to securely and conveniently manipulate nucleus 28, by appropriate movement of cryomanipulator 50. When tip 72 is deactivated, using switch 62, the freeze-grip is released and tip 72 can be repositioned on a different region on nucleus 28 or on another tissue. Thus, by sequentially positioning, activating, repositioning and deactivating cryogenic tip 72, nucleus 28 can be efficiently and accurately manipulated during surgery.

Cryogenic tip 72 is cooled to a predetermined temperature, preferably on the order of −80° to −60° C., using a cryogenic gas such as carbon dioxide or nitrogen. The cryogenic gas is preferably supplied from a cryogenic gas source (not shown in the drawings) via conduits 58, which are preferably insulated from the external environment using an insulating layer 76, as is known in the art. Insulator 76 ensures that only tip 72 will be cooled to the cryogenic temperature upon supply of the cryogenic gas to conduits 58. The supply of cryogenic gas is preferably controlled by a valve which, in turn is controlled by switch 62, as described below with reference to FIG. 8.

As described above, in a preferred embodiment of the invention, surgical instrument 32 operates on region 33 while nucleus 28 is temporarily supported by cryomanipulator 50 at region 64. The freeze-grip between cryogenic tip 72 and region 64 provides a firm, stable support of nucleus 28, allowing convenient operation of surgical instrument 32.

Sleeve portion 54 includes an aperture 68, preferably having an "air collector" shaped as outlined in FIGS. 2 and 3, which surrounds cryogenic tip 72 of manipulator head 66. In one preferred mode of operation, described below, sleeve 54 supplies a stream 75 of a predetermined liquid to the vicinity of region 64, via aperture 68. In another preferred mode of operation described below, sleeve 54 collects intraocular tissue via aperture 68, preferably using a vacuum suction device. Thus, as described below, sleeve 54 is preferably associated with a pipe suction device, as are known in the art. In some preferred embodiment of the present invention, pipe 56 is connected to the liquid source and the vacuum device via a flow selector (not shown in the drawings) which enables convenient switching between the liquid supply mode and the vacuum suction mode. Preferably, the selector further includes an "OFF" mode in which the liquid source and vacuum device are both disconnected. In one preferred embodiment, the flow selector includes a three-way valve as is known in the art.

In the liquid supply mode, the liquid supplied to region 64 expedites the release of the freeze-grip when cryogenic tip 72 is deactivated, using switch 62. This enables quicker repositioning of tip 72, and, thus, improves the efficiency and accuracy of cryomanipulator 50. In some preferred embodiment, the flow selector includes a three-way valve as is known in the art.

In the liquid supply mode, the liquid supplied to region 64 expedites the release of the freeze-grip when cryogenic tip 72 is deactivated, using switch 62. This enables quicker repositioning of tip 72 and, thus, improves the efficiency and accuracy of cryomanipulator 50. In some preferred embodiments of the present invention, the liquid supply through aperture 68 may include a dissolving agent, as is known in the art, which assists in the surgical procedure.

In a preferred embodiment of the present invention, manipulator head 66 further includes a heating device 74, juxtaposed with cryogenic tip 72. Heating device 74, which may include a miniature heating element known in the art, is preferably activated when cryogenic tip 72 is deactivated, to further expedite the release of the freeze-grip, thereby to further improve the efficiency of cryomanipulator 50. Electric power to operate tip 74 is prefereably provided from an external power source (not shown in FIGS. 2 and 3), via electric conductors 60. Activation and deactivation of heating device 74 is preferably controlled by the surgeon using a switch 65, which is preferably located on body portion 52.

As further shown in FIGS. 2 and 3, manipulator head 66 preferably further includes a surgical tip 70, for example a nail-shaped blade mounted on sleeve 54, which assists in manipulating the intraocular tissue and/or in guiding cryogenic tip 72 to a desired position. Surgical tip 70 can also be utilized to perform a given surgical function, for example cutting or breaking of the tissue in lens 20. The shape and structure of surgical tip 70 is preferably designed in accordance with specific surgical requirements. For example, tip 70 may have a "fingernail" shape as shown in the drawings, a "can-opener" shape, a "pin" or any suitable shape as is known in the art. Additionally, the surface of surgical tip 70 may be coated within abrasive coating (not shown) such as a diamond-dust coating.

Reference is now made also to FIGS. 4a and 4b which schematically illustrate, respectively, a cross-sectional top view and a cross-sectional front view of one preferred variation of cryomanipulator 50. In this preferred variation, conduits 58 include coaxial inner and outer conduits 84 and 82, respectively, separated by a barrier 88. Insulator layer 76 covers the entire external surface 86 of conduit 82, except for an exposed region defining tip 72. In the example shown in FIG. 4A, inner conduit 84 functions as an inlet for the cryogenic gas and outer conduit 82 functions as an outlet for the cryogenic gas. As shown in FIG. 4B, conductors 60 and liquid-supply/suction pipe 56 are both mounted above the conduits and pipe 56 is mounted below the conduits.

As shown particularly FIG. 4A, sleeve 54 is preferably mounted to body portion 52 using a bayonet structure including an outer connector 80 on sleeve 54 and an inner connector 78 on body portion 52. This enables simple removal of sleeve 54, e.g., for cleaning and/or for replacement by a different sleeve, or a different mounting configuration, as explained below with reference to FIGS. 6 and 7.

Reference is now briefly made to FIGS. 5A and 5B which schematically illustrate, respectively, a cross-sectional top view and a cross-sectional front view of another preferred variation of cryomanipulator 50. In this preferred variation, conduits 58 include folded conduit segments 94 and 92, having edges 96. Segments 94 and 92 are preferably cast in insulating material 98 which covers the entire external surface of edges 96 except for the exposed region defining tip 72. In the example shown in FIG. 5A, segment 94 functions as an inlet for the cryogenic gas segment 92 functions as an outlet for the cryogenic gas. As shown in FIG. 5B, conductors 60 and liquid-supply/suction pipe 56 are both mounted along conduit segments 92 and 94. Preferably, conductors 60 are mounted above the segments and pipe 56 is mounted below the segments.

Reference is now made to FIGS. 6 and 7 which are schematic side view illustrations of two respective, preferred, mounting configurations of sleeve 54 on body portion 52, using bayonet connectors 78 and 80. In the configuration of FIG. 6, surgical tip 70 is situated above cryogenic tip 72 and the "air collector"-shaped aperture 68 is below tip 72. The appropriate mounting configuration for sleeve 54 is preferably selected by the surgeon in accordance with other specific surgical tasks of manipulator head 66. In other preferred embodiments of the present invention (not shown in the drawings), sleeve 54 may be replaced by different types of sleeves which are selected in accordance with specific surgical requirements. For example, the replacement sleeves may include sleeves having different types of surgical tips 70, as described above.

As further shown in FIGS. 6 and 7, liquid-supply/suction pipe 56 preferably extends along conduits 58 only in body portion 52 and not in sleeve 54, i.e., pipe 56 ends substantially in line with bayonet connectors 78 and 80. Thus, in the liquid supply mode described above, the liquid supplied from pipe 56 is distributed substantially homogeneously around tip 72 at aperture 68. This ensures that the supplied liquid covers the entire contact region 64.

Figure 8:
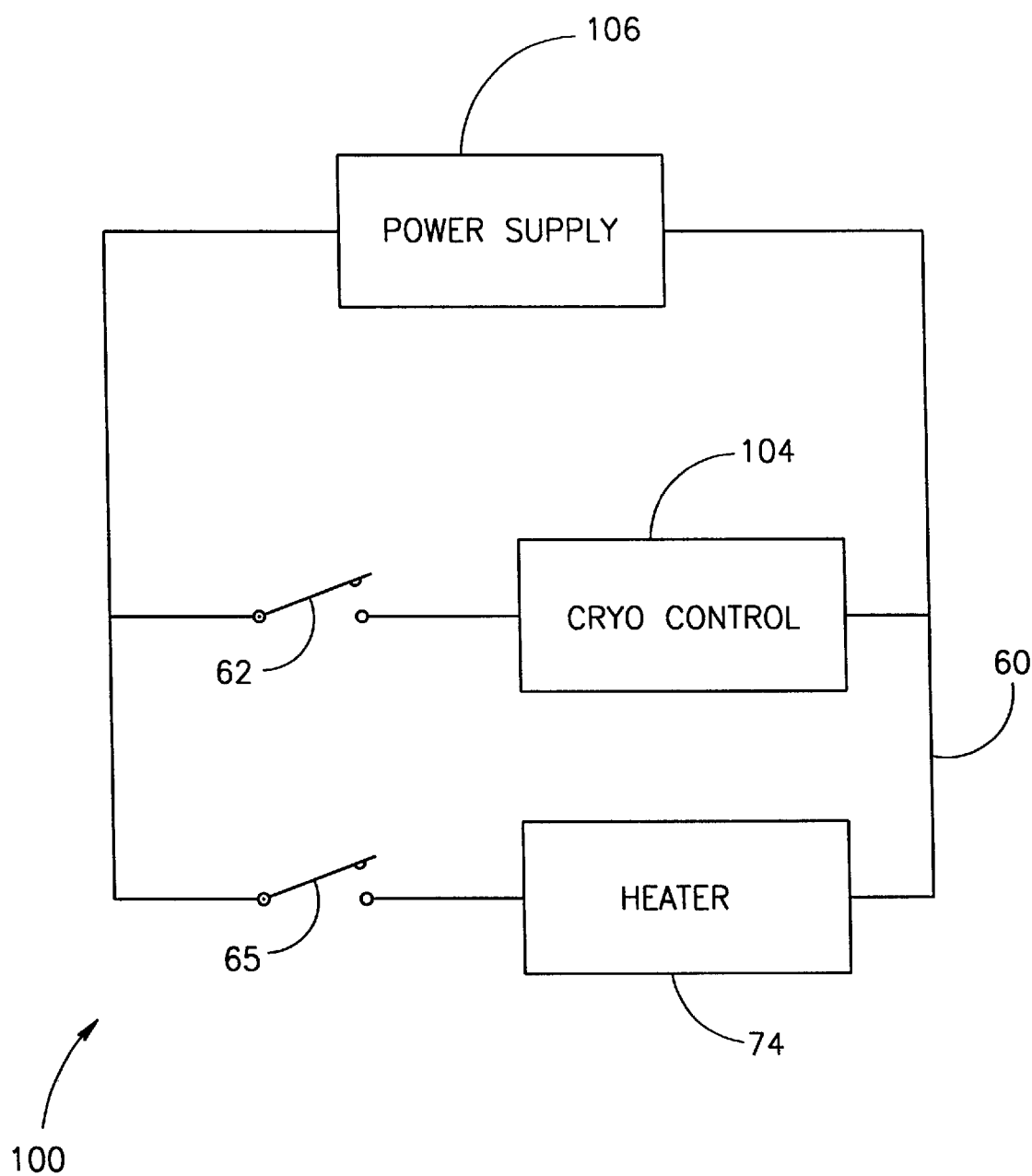
FIG. 8 is a schematic illustration of a preferred electrical circuit for the cryomanipulator of FIG. 2.

Reference is now made to FIG. 8 which schematically illustrates a preferred electrical circuit 100 for cryomanipulator 50. Circuit 100 includes a cryogenic controller 104 and heater 74 which are preferably connected to a power supply 106 via activating switches 62 and 65, respectively, and conductors 60. Power supply 106 preferably includes a low voltage DC power supply such as a battery or an appropriate AC/DC converter/transformer. Cryogenic controller 104, which preferably includes a valve (not shown) on conduits 58 (FIGS. 2–7), controls the supply of cryogenic gas to tip 72 via conduits 58. The operation of heater 74 has been described above with reference to FIGS. 2 and 3.

Figure 9:
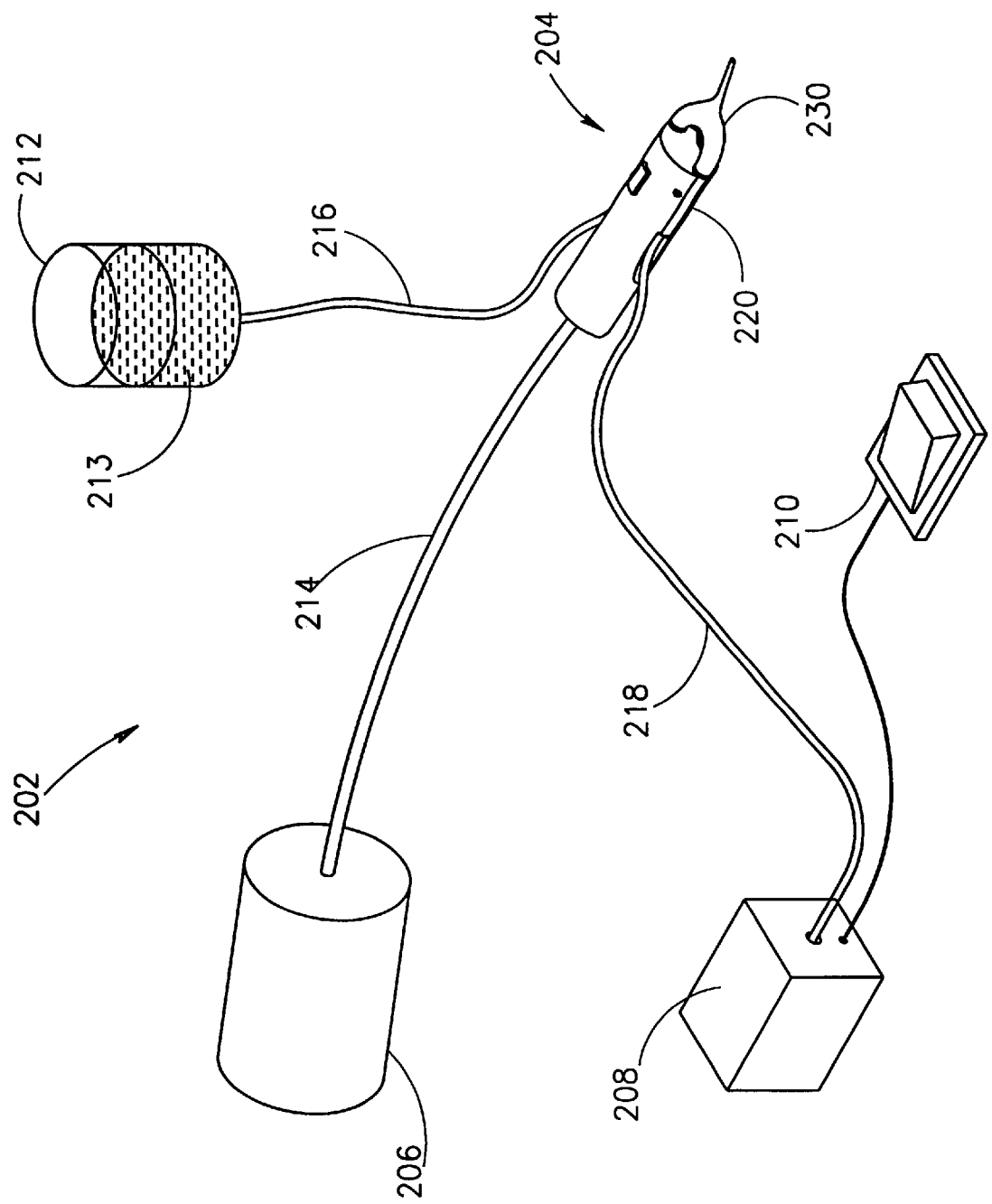
FIG. 9 is a schematic isometric view of a system for removing cataract in accordance with a preferred embodiment of the present invention.

Reference is now made to FIG. 9 which is a schematic isometric view illustrating a cataract removing system. The cataract removing system 202 includes a hand held cataract removing device (CRD) 204, a motor 206 for powering the CRD 204, a reservoir 212 for supplying a sterile physiological irrigation solution 213 to the cataract removing device 204, a vacuum pump 208 for providing reduced pressure at the tip of the CRD 204 and a foot pedal 210 for controlling the action of the vacuum pump 208.

The motor 206 is a variable speed electrical motor which is detachably connected to the CRD 204 by a flexible shaft 214 for supplying rotary power to the CRD 204. The motor 206 also includes a suitable control cable (not shown for the sake of clarity of illustration) which connects the motor 206 with the CRD 204 to enable CRD 204 to control the rotation speed of the motor 206. The motor 206 also includes the control circuits (not shown) for controlling the rotary speed of the motor 206.

The reservoir 212 is connected by tubing 216 to the CRD 204 for supplying the sterile irrigation physiological solution 213 to the CRD 204. The reservoir 212 can be a standard sterile infusion bag having tubing 216 built-in. The rate of flow of the irrigation solution 213 can be controlled gravitationally by adjusting the height of the reservoir 212 above the level of the CRD 204. Alternatively, the rate of flow of the irrigation solution 213 can be controlled by other means of flow control such as the standard flow regulating constricting device which is usually built into standard commercially available infusion-bag tubing (not shown) or an adjustable speed peristaltic pump (not shown).

The vacuum pump 208 can be any suitable vacuum pump or other suitable device for providing reduced pressure. The vacuum pump 208 is connected to the CRD 204 by a tubing 218. Alternatively, in cases where a centrally supplied vacuum is available tubing 218 can be suitably connected to the vacuum inlet, obviating the need for vacuum pump 218. The tubing 218 can be any suitable flexible tubing that can operate under reduced pressure. Pump 218 is suitably connected to foot-pedal 210 which controls the vacuum pump 208.

The CRD 204 includes a handle 220 and a disposable drilling unit 230 which is connectable to the handle 220.

Reference is now made to FIGS. 10A, 10B, 11 and 12 illustrating the structure of the handle 220 and the drilling unit 230 in detail.

FIG. 10A is a schematic isometric view illustrating the cataract removing device (CRD) of the cataract removing system of FIG. 9 and FIG. 10B is a schematic isometric view illustrating in detail the tip of the disposable drilling unit which is part of the CRD of FIG. 10A.

The handle 220 is a rod-like handle having two hollow cylindrical passages 226 and two recesses 254 therewithin. The handle 220 also includes a rotatable coupler 228 which is suitably connected to the motor 206 by the flexible shaft 214, which passes through the handle 220. Thus, when the motor 206 is operating the rotatable coupler 228 is rotated by the flexible shaft 214. The flexible shaft 214 can be structurally integrated within the handle 220 and directly connected to the coupler 228. Alternatively, coupler 228 can be connected to a separate axle (not shown) which is detachably connected to the flexible shaft 214. In the latter case the flexible shaft 214 can be detached from the handle 220 to facilitate the sterilization thereof.

The handle 220 also includes a controlling unit 224 (FIG. 10A) for manually controlling the speed of rotation of the motor 206. The controlling unit 224 can be any suitable switch for enabling the starting and stopping of the motor 206 and for controlling the speed of rotation thereof. The handle 220 can be made of any suitable material which is sterilizable, such as a metal or a durable plastic.

FIG. 11 is a schematic top view of the CRD 204 of FIG. 10A illustrating the disposable drilling unit 230 assembled with the handle 220 of the CRD 204. The drilling unit 230 is roughly Y shaped as best seen in FIG. 11. As best seen in FIG. 10A, the drilling unit 230 has two hollow tubular members 240 at its end proximal to the handle 220, and a middle part 241 which tapers at its end distal from the handle 220, forming a distal shaft 242. Each tubular member 240 has a notch 236 therein (FIG. 10A) and has a fluid conduit 256 (FIG. 11) passing therethrough. Each tubular member 240 also includes a sealing gasket 238 suitably mounted thereupon. Each of the sealing gaskets 238 abuts the middle part 241. The fluid conduits 256 continuously taper within the middle part 241 (FIG. 11) extending therethrough to the tip of the distal shaft 242, where they each end in an orifice 250 (FIG. 10B). The drilling unit 230 also includes a drill axle 248 which passes through a cylindrical axle channel 249 (FIG. 12). The axle channel 249 extends through the middle part 241 and the distal shaft 242 of the drilling unit 230 and is positioned between the fluid conduits 256. The drill axle 248 is connected to a drill blade 246 (FIG. 10B) and to a coupler 232, thus forming a drill. The distal shaft 242 includes a guard lip 244 which extends under the drill blade 246 (FIG. 10A).

It is noted that the CRD 204 is designed for disintegrating a lens or cataract of the eye which has been converted from its gel-like state into a solid-like state. The lens can be converted into a solid state by freezing it into an ice-like consistency by any suitable method of freezing, such as freeze-gripping by any of the embodiments of the cryomanipulator disclosed hereinabove. However, any other suitable method for converting the lens into a solid-like state can be used to enable the use of the CRD of the present invention. When the lens is frozen or in a solid-like state, the drill blade 246 of the drilling unit 230 can effectively break (disintegrate) the cataract.

It is also noted that the drilling unit 230 can be made of any suitable material. For example, the drilling unit 230 can preferably be made of sterilizable non-pyrogenic plastic. It is also noted that the axle 248 and the drill blade 246 can be made of any suitable material, such as surgical steel or stainless steel.

FIG. 12 is a schematic cross section of the disposable drilling unit of FIG. 11 along the line XII—XII illustrating two fluid conduits 256 passing within the drilling unit 230, It is noted that, although the two fluid conduits 256 passing within the drilling unit 230 are shown to be structurally similar to each other (FIGS. 11 and 12), they can also be of different dimensions. For example, the part of one of the two fluid conduits 256 which passes within the distal shaft 242 may have a larger diameter than the corresponding part of the other fluid conduit 256. Thus, the diameters of the orifices 250 which are shown to be equal in FIG. 10B, can also be of different dimensions. For example, the orifice 250 which is used for irrigation can have a larger diameter than the orifice 250 which is used for aspiration, mutatis mutandis.

Reference is now made to FIG. 13 is a schematic side view of the CRD 204 of FIG. 11 illustrating the disposable drilling unit 230 assembled with the handle 220 of the CRD 204. Each of the tubes 216 and 218 includes a hollow adapter 222 suitably attached thereto. The adapter 222 of tubing 216 can be sealingly fitted into one of the passages 226 for providing irrigation fluid to one of the orifices 250 of the drilling unit 230 through one of the conduits 256. The adapter 222 of tubing 218 can be sealingly fitted into the remaining passage 226 for providing reduced pressure at the distal shaft 242 of the drilling unit 230, thus removing excess irrigation fluid by aspiration thereof at the second orifice 250 through the other conduit 256.

The handle 220 also includes two spring and ball latches 252. Each spring and ball latch 252 is attached within the handle 220 in such a way that the ball 237 of the spring and ball latch 252 slightly protrudes into the cylindrical space of the passage 226.

The drilling unit 230 is connected to the handle 220 by inserting the tubular members 240 of the drilling unit 230 into the passages 226 of the handle 220 and pushing until the balls 237 of both spring and ball latches 252 lock within the notches 236 of the tubular members 240. For removing the drilling unit 230 from the handle 220, the drilling unit 230 and the handle 220 are pulled apart, disengaging the balls 237 from the notches 236.

When the two tubular members are locked within the passages 226 by the spring and ball latches 252, the couplers 228 and 232 are engaged so that when the coupler 228 is rotated by the axle 227, the coupler 232 also rotates. The coupler 232 thus rotates the axle 248 and the drill blade 246 of the drilling unit 230. Additionally, when the two tubular members are locked within the passages 226 by the spring and ball latches 252, the sealing gaskets 238 are pressed against the surface of the handle 220 sealing the connection between the drilling unit 230 and the handle 220. Thus, the sealing gaskets 238 prevent leakage of irrigation fluid from passages 226. The sealing gasket 238 also prevents penetration of atmospheric air into the passage 226 connected to the tubing 218, thus, preventing pressure equalization between the conduit 256 which is connected to the vacuum pump 208 and the air outside the CRD 204.

The couplers 228 and 232 are conical in shape and can be made from any suitable material such as synthetic rubber or a similar resilient material. Thus, when the drilling unit 230 is latched within the handle 220, the couplers 228 and 232 are slightly pressed one against the other and are thus mechanically coupled by friction. This arrangement has the advantage that if the drill blade 246 is accidentally stopped from rotating by contacting a hard object such as the cryomanipulator tip 72 or any other hard object, the breakage or twisting of the axle 248 is prevented since coupler 228 will slide against the static coupler 232.

It is noted that, although the couplers 228 and 232 of the preferred embodiment of the present invention are shown as conical in shape and made of synthetic rubber, they can be made in other shapes and of other materials. For example, the couplers 228 and 232 can have a spherical shape or a hemispherical shape or any other shape suitable for rotatably coupling the couplers 228 and 232 together. If the couplers 228 and 232 are spherically or hemispherically shaped (not shown), they can be rotatingly engaged at a multiplicity of different angles, in contrast to conical couplers which can be effectively coupled at specific predetermined angles. Thus, spherically or hemispherically shaped couplers can have an advantage over conical couplers in implementations where the handle 220 needs to be couplable to different drilling units, each having a coupler that is oriented at a different angle to the coupler of the handle 220.

Additionally, the method of coupling of the couplers 228 and 232 can be any suitable method of rotational coupling. For example the couplers 228 and 232 can be conical cogwheels or any other suitable type of cogwheels.

It is also noted that, the couplers 228 and 232 can be differently shaped and can be made of a different materials. For example, coupler 228 can be conical in shape and made of plastic and coupler 232 can be hemispherical in shape and made of synthetic rubber. It is also noted that, since the drilling unit 230 is disposable, the coupler 232 can be made of a material which is less durable than the coupler 228.

When the CRD 204 is assembled for use in a cataract operation, the two hollow adapters 222 of the tubing 216 and 218 are inserted into the two passages 226 and the drilling unit 230 is assembled by inserting the tubular members 240 into the passages 226 and latching the drilling unit 230 in place as described hereinabove. The surgeon starts the operation of the vacuum pump 208 and adjusts the rate of flow of the sterile irrigation physiological solution 213 at the tip of the distal shaft 242 of the drilling unit 230. The surgeon makes two small incisions at the sciero-corneal region of the eye. The incisions can be regular incisions or can be made using the "tunnel" technique. The tunnel technique is the prior art technique of forming a passage through the tissue of the sclero-corneal region of the eye to create a "self-sealing" passage into the eye. The surgeon then forms two tracts extending from the incisions through the anterior chamber of the eye to the anterior capsule. The surgeon then inserts a cryomanipulator through the first incision and first tract into the anterior chamber of the eye. The surgeon also inserts the distal shaft 242 of the drilling unit 230 of the CRD 204 through the second incision and second tract into the anterior chamber of the eye under visual control using a stereoscopic microscope. The surgeon further makes at least one opening in the anterior capsula of the lens. The opening is made before the insertion of the cryomanipulator and the CRD into the lens.

Figure 14:
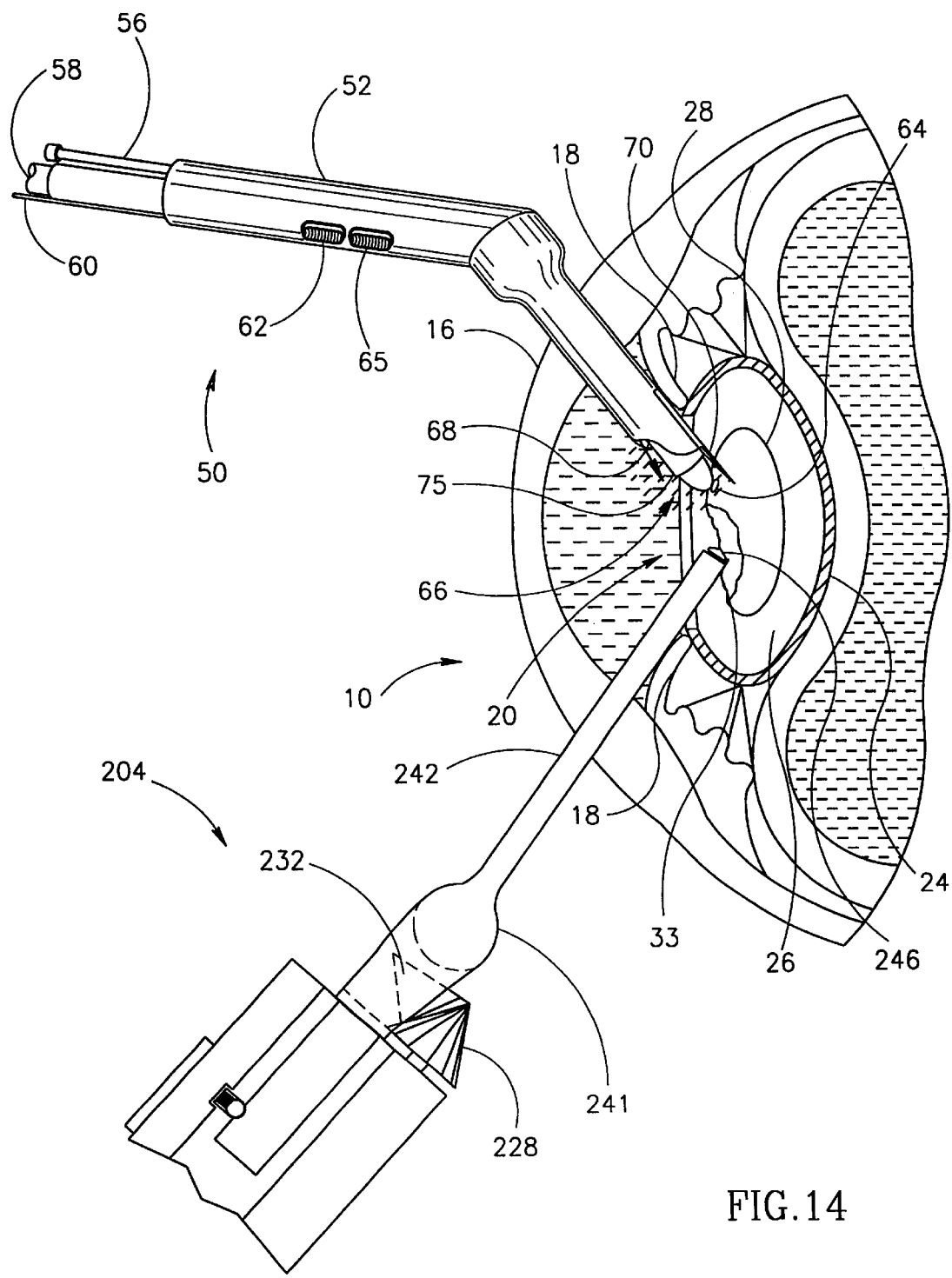
FIG. 14 is a schematic, side view, partly cross-sectional illustration of a human eye during cataract surgery, illustrating the cryomanipulator and the CRD positioned within the eye, in accordance with another preferred embodiment of the present invention.

FIG. 14, to which reference is now made, is a schematic, side view, partly cross-sectional illustration of a human eye during cataract surgery, illustrating the cryomanipulator 50 and the CRD 204 positioned within the eye, in accordance with another preferred embodiment of the present invention. The surgeon inserts the cryogenic tip 72 of the cryomanipulator head into the lens and places the tip 72 in contact with the nucleus of the cataract at the region of contact 64. The surgeon freeze-grips the nucleus with the cryomanipulator. The nucleus is at least partially frozen into a solid-like state by the cryomanipulator.

When the tip of the distal shaft 242 of the CRD 204 is correctly positioned relative to the frozen nucleus, the surgeon switches the motor 206 on by using the controlling unit 224 of the handle 220 and uses the controlling unit 224 for controlling the speed of rotation of the drill blade 246. The surgeon uses the drill blade 246 to break (disintegrate) the frozen nucleus under visual control, while the nucleus is being held fixed to the tip 70 of the cryomanipulator 50. The fragments of the cataract which are broken off by the drilling action of the drill blade 246 are continuously washed out by the irrigation physiological solution 213 which flows out of one of the orifices 250 and removed by aspiration through the other orifice 250. The rate of aspiration can be controlled by the surgeon by using the foot pedal 210 which in turn, controls the reduced pressure created by the suction pump 208.

It is noted that, in contrast to the use of an ultrasonic probe such as the "Phaco", the area of the cataract which is being affected by the drill blade 246 is clearly visible during the operation. An additional advantage of the present invention is that the guard lip 244 at the tip of the distal shaft 242 protects the tissue directly underneath the drill blade 246 from being accidentally damaged if the distal shaft 242 is inadvertently moved downwards. An important feature of the guard lip 244 is that when the distal shaft 242 is advanced into the frozen tissue, the drill blade 246 drills a hole (not shown) in the tissue until the guard lip 244 touches the frozen tissue preventing further drilling in the initial drilling direction. In order to continue the drilling the surgeon must readjust the drilling direction to enable the guard lip 244 to be inserted into the initially drilled hole. Thus, the distal shaft 242 must be moved in a direction suitable for enabling the insertion of the guard lip 244 into the drilled hole, thus during the drilling of the nucleus the distal shaft is gradually moved away from the posterior capsula . This feature helps in protecting the posterior capsula from being accidentally damaged while the parts of the cataract adjacent to the posterior capsula are removed. After the cataract has been completely removed, an artificial lens can be introduced. The cryomanipulator and the distal shaft 242 of the drilling unit 230 are then taken out of the eye through the incisions. The surgeon disposes of the used drilling unit by pulling it out of the handle 220.

It is further noted that, when the CRD 204 is assembled from the handle 220 and the drilling unit 230, the distal shaft 242 is inclined at an angle relative to the handle 220. A variety of different drilling units (not shown) can be made, each different drilling unit producing a different angle between the handle 220 and the distal shaft 242, in the assembled CRD, so that the surgeon can select a drilling unit which is suitable for a specific operation or which is most convenient for him to operate.

Figure 15:
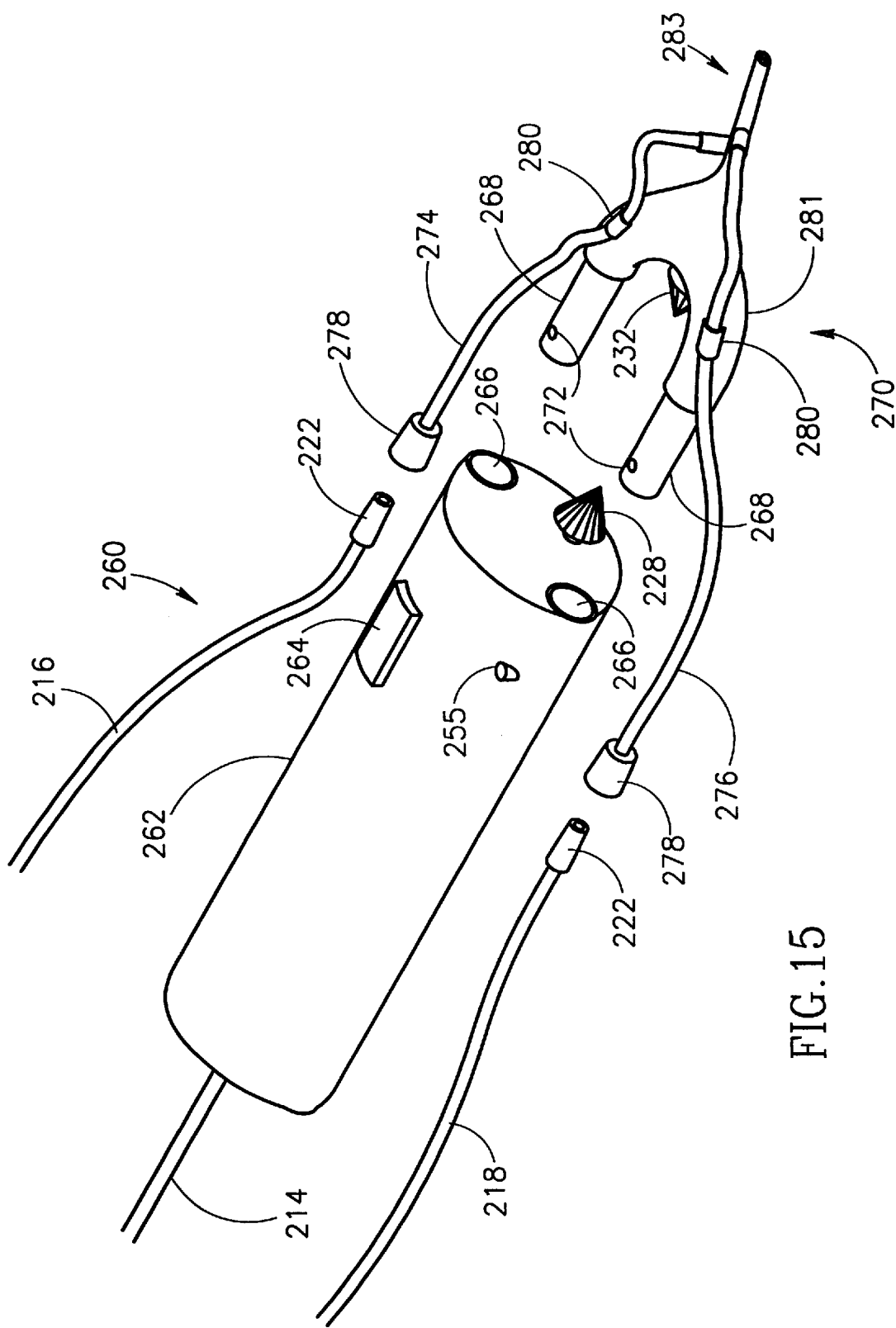
FIG. 15 is a schematic isometric view illustrating a different CRD in accordance with an additional preferred embodiment of the present invention.

Reference is now made to FIG. 15 which is an isometric view illustrating a CRD 260 in accordance with another preferred embodiment of the present invention having a drilling unit 270 in which one of the fluid conduits is positioned within the other fluid conduit. The CRD 260 can be used similarly to the CRD 204 in the cataract removing system of FIG. 9.

The CRD 260 includes a hand held handle 262 and a disposable drilling unit 270. The handle 262 includes two cylindrical cavities 266 therewithin. The handle 262 also includes two spring and ball latches 255 . The spring and ball latches 255 of the handle 262 are similar in construction and operation to the spring and ball latches 252 of the handle 220. The handle 262 also includes a controlling unit 264 similar to the controlling unit 224 of the handle 220 of the CRD 204. The handle 262 also includes a flexible shaft 214 and a coupler 228 as described in detail for the handle 220 of the CRD 204 and illustrated in FIG. 10A hereinabove.

The drilling unit 270 includes two cylindrical members 268 each having a notch 272 therein, for receiving the ball of the spring and ball latch 255 therewithin. The drilling unit 270 is assembled with the handle 262 as disclosed in detail hereinabove for the drilling unit 230 and the handle 220, respectively. The drilling unit 270 further includes a middle part 281 and a distal shaft 283. The drilling unit 270 also includes two flexible tubes 274 and 276 for providing irrigation fluid and reduced pressure to the distal shaft 283, respectively. Each of the tubes 274 and 276 is connected to the distal shaft 283 at one end and to a hollow adapter 278 at the other end.

The hollow adapters 278 are connectable to the adapters 222 of the tubes 216 and 218. The tubes 274 and 276 are secured to the middle part 281 of the drilling unit 270 by retainers 280. The tubes 274 and 276 are connected to the tubing 216 and 218 of the cataract removing system 202 of FIG. 9 for supplying irrigation fluid and reduced pressure to the drilling unit 270 as disclosed in detail for the drilling unit 230 hereinabove.

Figure 16:
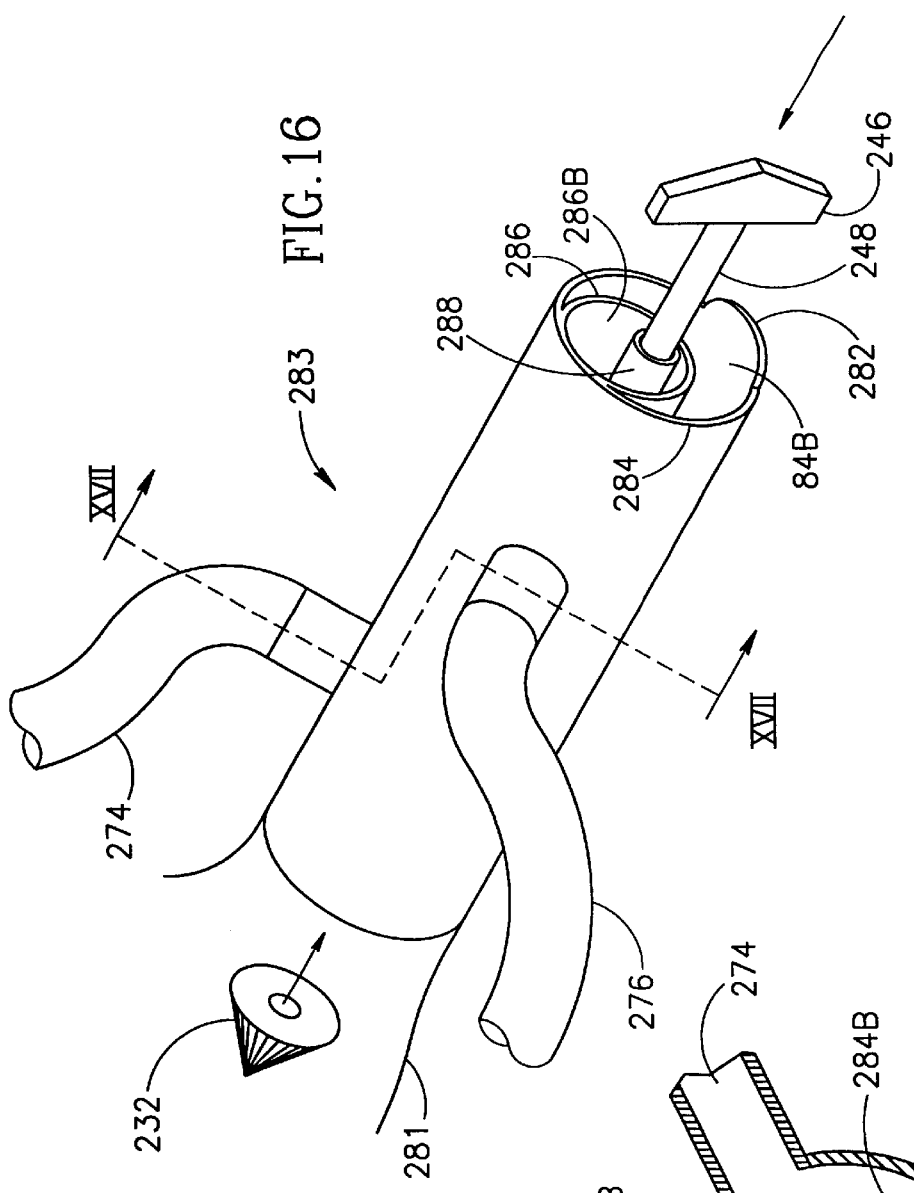
FIG. 16 is a schematic, exploded, isometric view of part of the disposable drilling unit of the CRD of FIG. 15.
Figure 17:
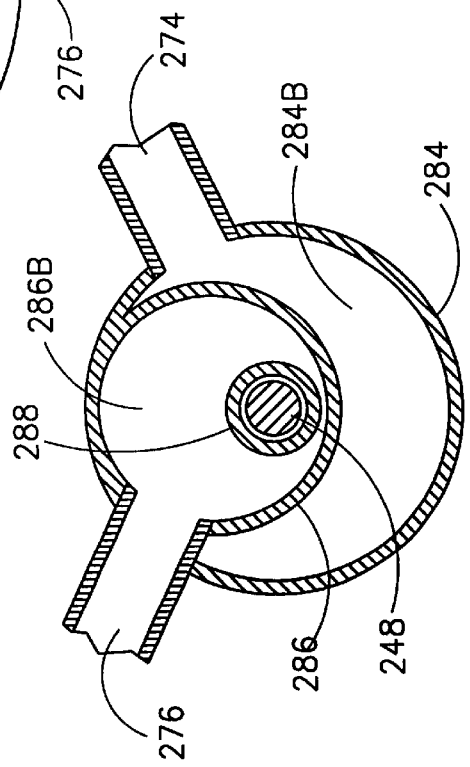
FIG. 17 is a schematic cross section of the distal shaft 83 of FIG. 16 taken along the lines XVIIB—XVIIB.
Figure 18:
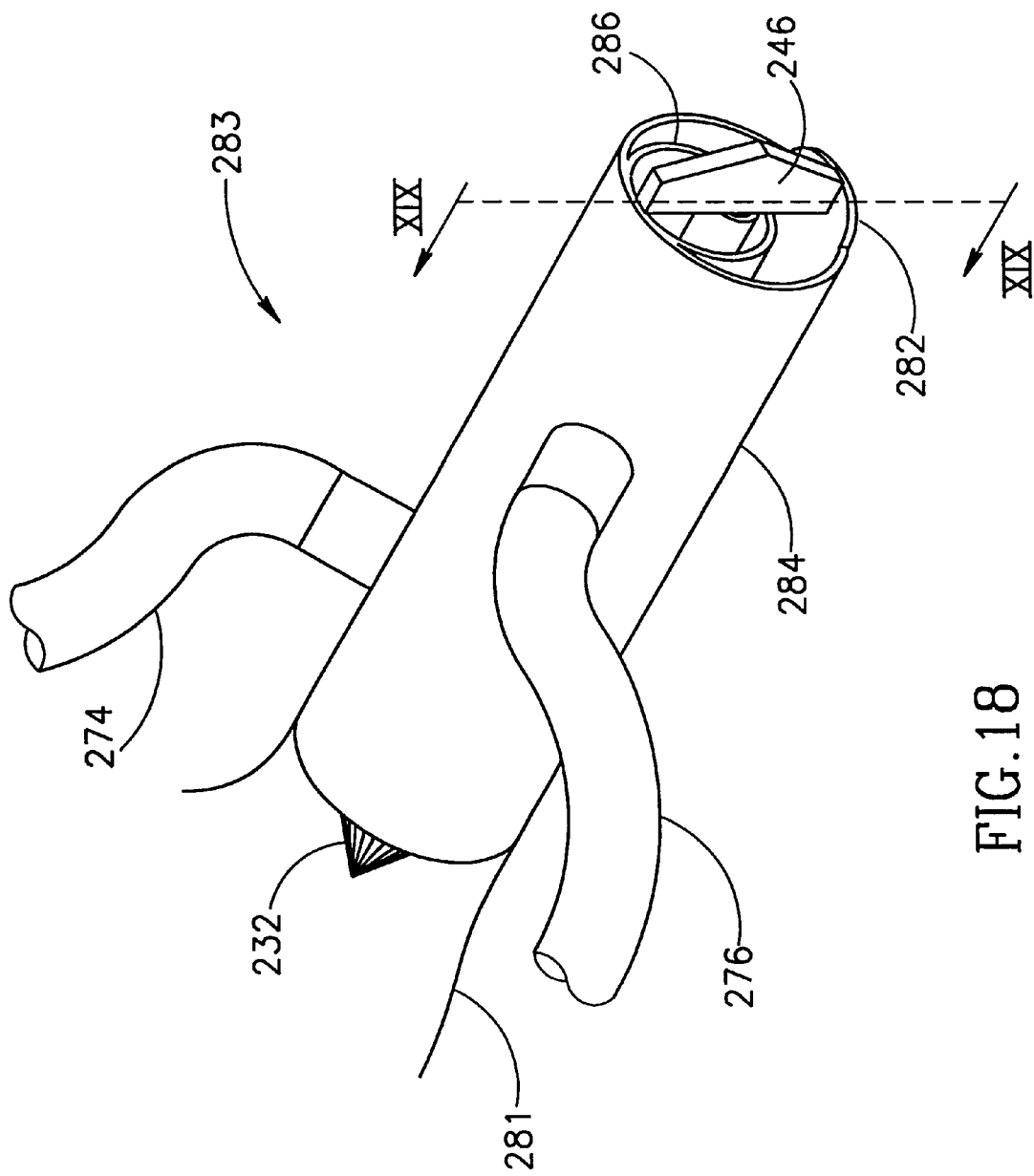
FIG. 18 is a schematic isometric view of part of the drilling unit of the CRD of FIG. 15.
Figure 19:
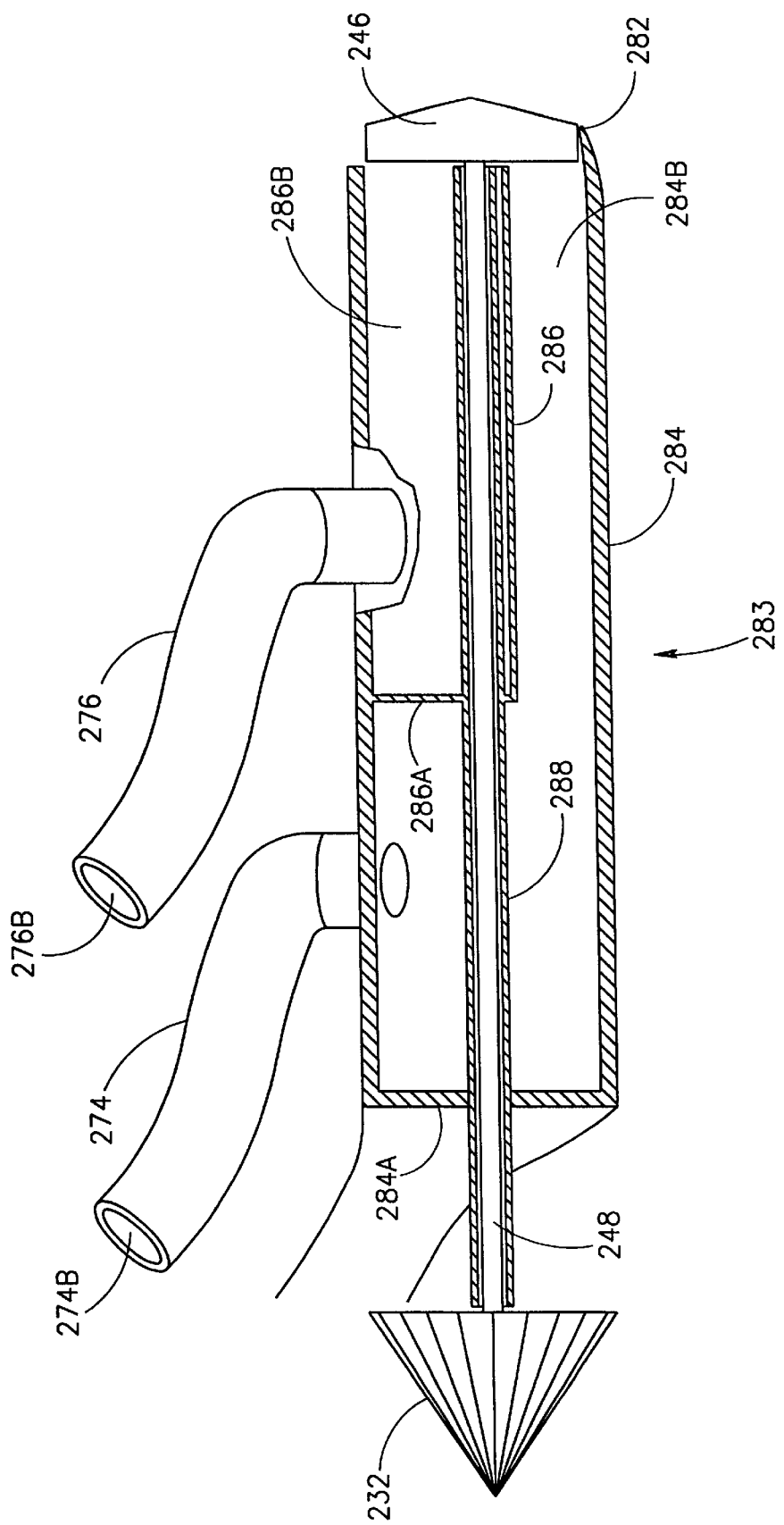
FIG. 19 is a schematic cross section of the distal shaft of the drilling unit of FIG. 18 along the lines XIX—XIX.

Reference is now made to FIGS. 16–19. FIG. 16 is an exploded isometric view illustrating a part of the drilling unit 270 in detail. FIG. 17 is a schematic cross section of the distal shaft 283 of FIG. 16 taken along the lines XVII—XVII thereof. FIG. 18 is a schematic isometric view of the distal shaft 283 of the drilling unit 270 of FIG. 15. FIG. 19 is a longitudinal cross-section of the distal shaft 283 of FIG. 17 taken along the lines XIX—XIX.

The distal shaft 283 of the drilling unit 270 of FIG. 16 includes a cylindrical tube 284 having one closed end 284A (best seen in FIG. 19) which is attached to the middle part 281 of the drilling unit 270. The tube 284 includes a guard lip 282 (best seen in FIG. 18) extending at its open end and having a similar function to the guard lip 244 of FIG. 10B. The distal shaft 283 also includes a cylindrical tube 286 which is smaller in diameter than the cylindrical tube 284. The cylindrical tube 286 is shorter than the tube 284 and has one closed end 286A (FIG. 19). The tube 286 is positioned inside the tube 284 and attached thereto in such a manner that the longitudinal axes (not shown) of the tubes 284 and 286 do not coincide (FIG. 17). The distal shaft 283 further includes a cylindrical tube 288 which is smaller in diameter than tube 286 and is open at both ends (FIG. 19). The tube 288 is positioned within the tube 286 and attached thereto in such a manner that the longitudinal axis (not shown) of the tube 288 coincides with the longitudinal axis (not shown) of the tube 284 (FIG. 17). The tube 288 passes through the closed ends 284A and 286A of the tubes 284 and 286, respectively, and is sealingly attached to the ends 284A and 286A (FIG. 19). Thus, the distal shaft 283 contains therewithin two separate fluid conduits 284B and 286B.

The distal shaft 283 also includes a drill axle 248 passing within the tube 288. The drill axle 248 can freely rotate within the tube 288. The drill axle 248 is connected to a drill blade 246 at one end and to a coupler 232 at the other end, thus forming a drill, as best seen in FIG. 19. The tubes 274 and 276 are connected to the tubes 284 and 286 in such a way that the fluid conduit 284B is continuous with the internal space 274B of the tubing 274 and the fluid conduit 286 is continuous with the internal space 276B of the tubing 276. Thus, when the CRD 260 replaces the CRD 204 in the cataract removing system 201 of FIG. 9, irrigation fluid can be supplied to the fluid conduit 284B by tubing 216 and reduced pressure can be supplied to fluid conduit 286B by tubing 218. Alternatively, irrigation fluid can be supplied to the fluid conduit 286B by tubing 216 and reduced pressure can be supplied to fluid conduit 284B by tubing 218 (not shown).

The CRD 260 is used in eye surgery for removing a cataract as disclosed in detail for the CRD 204 hereinabove.

Figure 20:
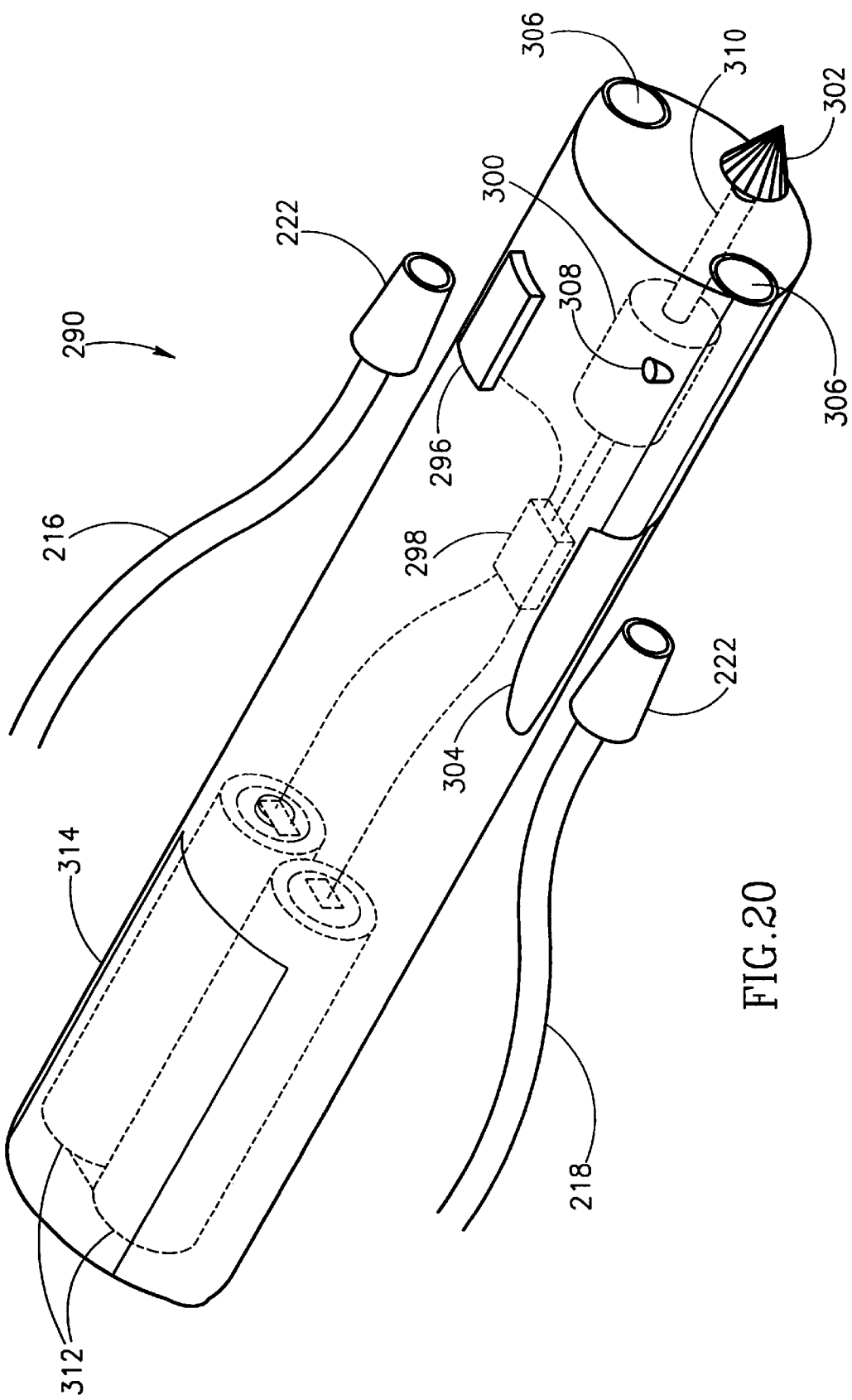
FIG. 20 is a schematic isometric view illustrating in detail a battery powered handle of a CRD, in accordance with another preferred embodiment of the present invention.

Reference is now made to FIG. 20 illustrating a handle 290 having an internal power source and motor in accordance with a preferred embodiment of the present invention.

The handle 290 can be connected to the drilling unit 230 of FIG. 10A instead of the handle 220. The handle 290 is similar to the handle 220 of FIG. 10A except that, instead of being connected to the external motor 206 of FIG. 9, the handle 290 includes an internal motor 300 suitably connected to an electrical power source 212 through a control unit 298. The electrical power source 312 can be a suitable electrical battery, such as a disposable battery, a rechargeable battery or a power supply connected to the standard alternating current mains socket (not shown). A removable cover 314 enables the replacement of the power source 312. The control unit 298 is connected to a controlling unit 296 for switching the motor 300 on and off and for controlling the speed of rotation of the motor 300. The motor 300 is suitably connected to an axle 310 which is connected to a coupler 302 similar to the coupler 228 of the handle 220. When the controlling unit 296 is switched on, the motor 300 rotates the axle 310 which rotates the coupler 228. The handle 290 also includes two hollow cylindrical passages 306, two recesses 304 and two spring and ball latches 308 similar to the passages 226, the recesses 254 and the spring and ball latches 252 of handle 220, respectively. The handle 290 is typically easier to manipulate than the handle 220 since it is not connected to a flexible shaft.

It is noted that, the handle 262 of the CRD 260 can also be replaced by a handle (not shown) which has an internal power source 312 such as a the battery of the handle 290 and cylindrical cavities which are identical to the cylindrical cavities 266 of the handle 262.

Figure 21:
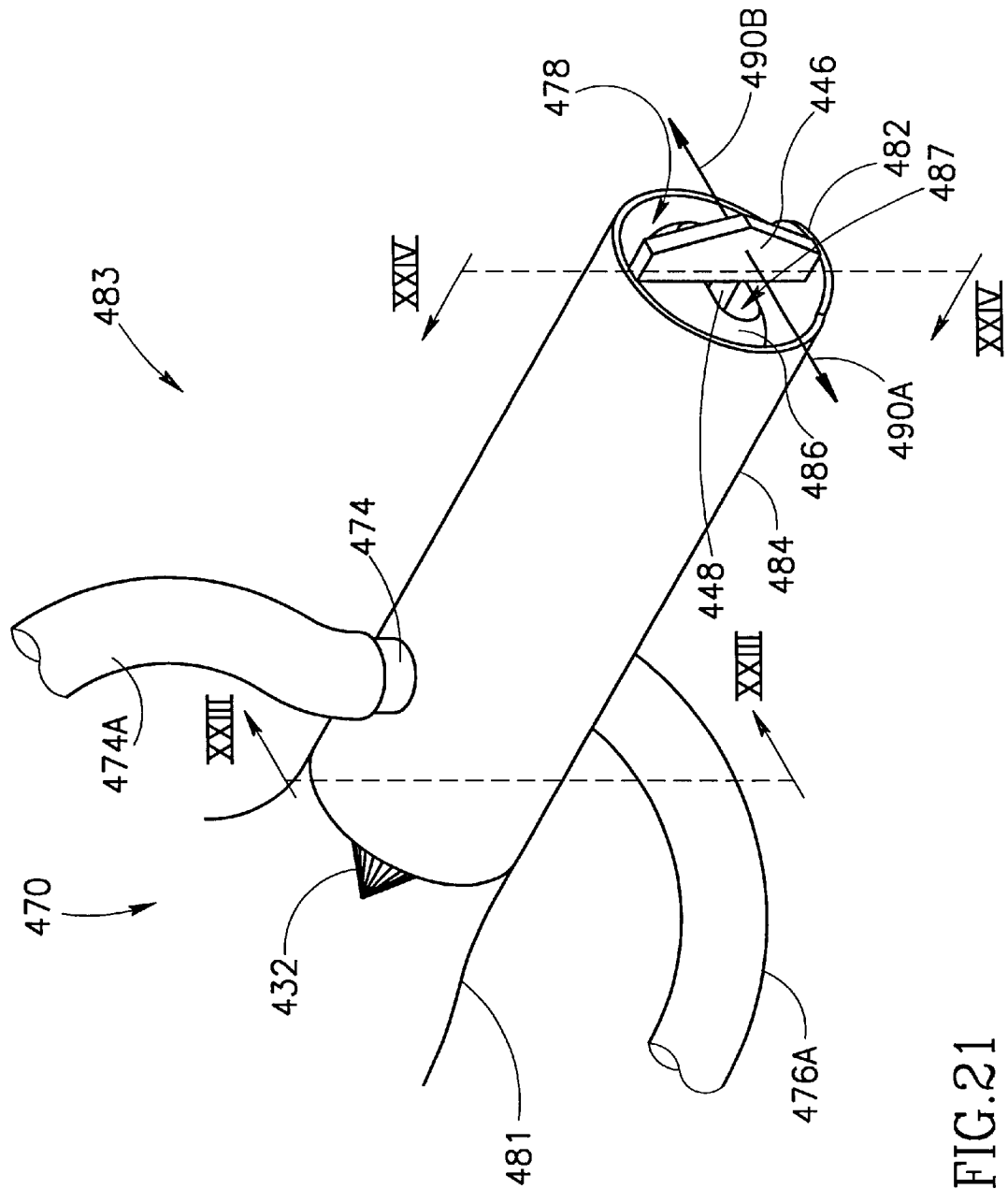
FIG. 21 is a schematic isometric view of part of anther drilling unit for use with the CRD of FIG. 15, in accordance with another preferred embodiment of the present invention.
Figure 22:
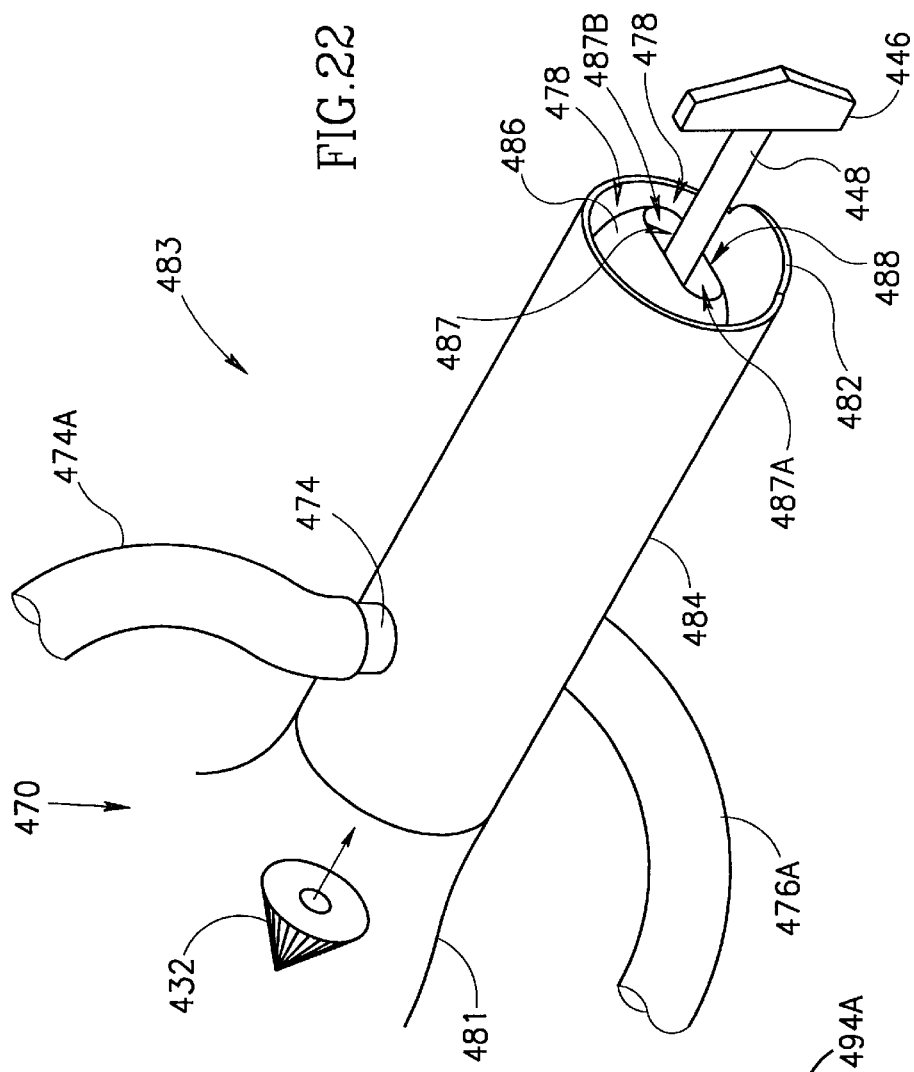
FIG. 22 is a schematic, exploded, isometric view of the part of the drilling unit of FIG. 21.
Figure 23:
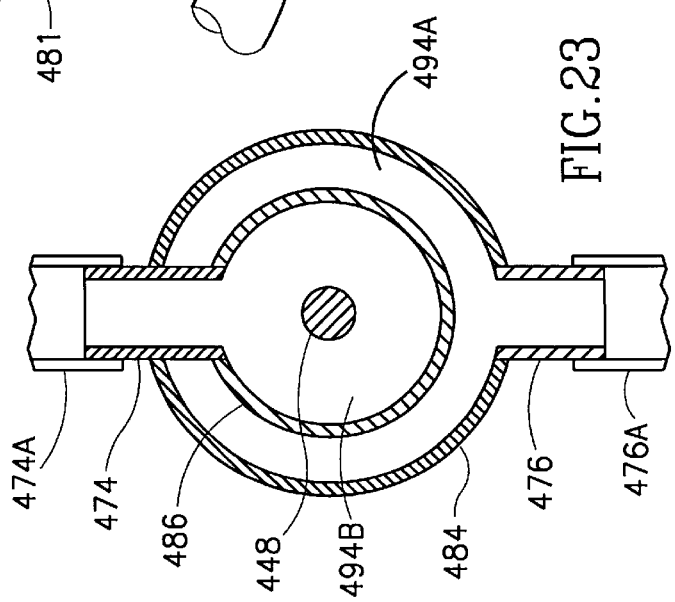
FIG. 23 is a schematic cross section of the part of the drilling unit of FIG. 21 along the lines XXIII—XXIII.
Figure 24:
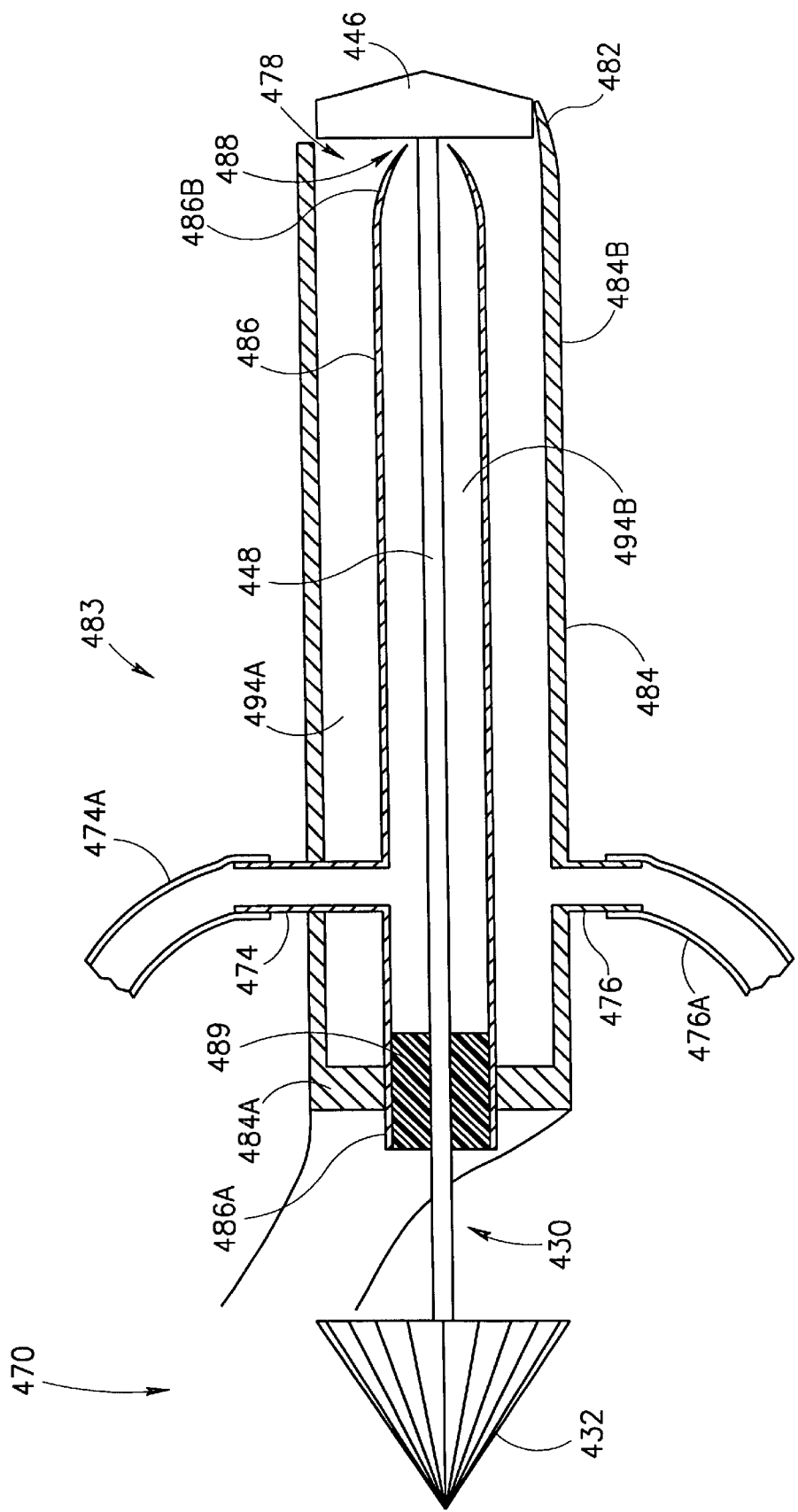
FIG. 24 is a schematic cross section of the part of the drilling unit of FIG. 21 along the lines XXIV—XXIV.

Reference is now made FIGS. 21–23. FIG. 21 is a schematic isometric view of part of another drilling unit for use with the handle 260 of FIG. 15, in accordance with another preferred embodiment of the present invention. FIG. 22 is an exploded, isometric view of the part of the drilling unit of FIG. 21. FIG. 23 is a schematic cross section of the part of the drilling unit of FIG. 21 along the lines XXIII—XXIII. FIG. 24 is a schematic cross section of the part of the drilling unit of FIG. 21 along the lines XXIV—XXIV.

The drilling unit 470 includes a housing comprised from two tubular members (not shown) similar to the two tubular members 240 of the drilling unit 270 of FIG. 10A, a distal shaft 483 and a middle part 481 connecting the hollow tubular members (not shown) with the distal part 483.

The drilling unit 470 is similar to the drilling unit 270 of FIG. 15 except that the distal shaft 483 of the drilling unit 470 of FIG. 21 is different from the distal shaft 283 of the drilling unit 270 of FIG. 16. The distal shaft 483 includes a first elongated hollow member 486 having a first portion 486A (best seen in FIG. 24) which is attached to the middle part 481 of the drilling unit 470 and a second portion 486B terminating in a slit-like first aperture 487 (best seen in FIGS. 22 and 24). While the first portion 486A of the first hollow member 486 is preferably of a uniform cross section, the second portion 486B of the first hollow member 486 progressively narrows or flattens towards the first aperture 487. Preferably, the thickness of the wall of the second portion 486B of the first hollow member 486 gradually diminishes towards the first aperture 487. Thus the second portion 486B of the first hollow member 486 forms a sharp cutting edge 488 defining the first aperture 487.

The first aperture 487 is preferably an elongated slit-like aperture having a first end 487A and a second end 487B (best seen in FIG. 22).

The distal shaft 483 also includes a second elongated hollow member 484 having a closed end attached to a middle part 481 of the drilling unit 470 and an open end 484B terminating in a second aperture 478. The second elongated hollow member 484 includes a guard lip 482 (best seen in FIGS. 23 and 24) extending beyond the second aperture 478 at the open end 484B of the second hollow member 484 and having a similar function to the guard lip 244 of FIG. 10B. The first hollow member 486 is disposed within the second hollow member 484. The first portion 486A of the first hollow member is attached to the closed end 484A of the second hollow member 484. The first hollow member 486 is positioned within the second hollow member 484 and attached thereto in such a manner that the longitudinal axis (not shown) of the first hollow member 486 coincides with the longitudinal axis (not shown) of the second hollow member 484 (FIG. 24). Thus, the distal shaft 483 contains therewithin two separate fluid conduits 494B and 494B.

The fluid conduit 494B communicates with a flexible tube 474A through a short tube 474 which is part of the first hollow member 486 and which sealingly passes through the wall of the second hollow member 484. The tube 474A may be used for connecting the fluid conduit 494B to a vacuum pump as disclosed in detail hereinabove. It is noted that the fluid conduit 494B may also be connected to the flexible tube 474A through a suitable short tube (not shown) passing through a passage (not shown) within the gasket 489, thus obviating the need for the tube 474.

The fluid conduit 494A communicates with a flexible tube 476A through a short tube 476 which is part of the second hollow member 484. The tube 476A may be used for connecting the fluid conduit 494A to a reservoir of suitable irrigation fluid as disclosed in detail hereinabove.

The distal shaft 283 also includes a drill shaft 448 passing within the first hollow member 486. The drill shaft 448 passes within a sealing gasket 489 sealingly attached within the first portion 486A of the first hollow member 486. The gasket 489 is made from Teflon, rubber, synthetic rubber, silicon rubber or any other suitable resilient material. The gasket 486 may also be implemented as a rigid metal disc with a circular hole, the hole being lined with a resilient gasket, positioned at any suitable point along the drill shaft 448. The drill shaft 448 can rotate within the gasket 489. If necessary, the seal between the drill shaft 448 and the gasket 489 may be improved by using a lubricating sealant such as a silicon grease or any other suitable sterilizable lubricating sealant. The drill shaft 448 is connected to a drill blade 446 at one end and to a coupler 432 at the other end, thus forming a drill bit 430 (FIG. 24). The drill bit 430 is coupled to a motor as disclosed in detail for the drilling units 230 and 270, hereinabove.

An advantage of the structure of the first hollow member 486 of the drilling unit 470 is that when the drilling unit 470 is used in conjunction with a handle such as the handle 262 of FIG. 15 for removing a cataract as disclosed in detail for the CRD 204 hereinabove, the drill shaft 448 can be moved within the slit-like aperture 487 between the first end 487A and the second end 487B of the slit by gently pushing the drill blade 446 against the frozen cataract and moving the distal shaft 483 in the directions which are generally perpendicular to the direction of the longitudinal axis (not shown) of the first hollow member 484. This moving will result in a reciprocating movement of the drill shaft 448 between the end 487A and 487B of the slit-like first aperture 487 in the directions represented by the arrows 490A and 490B (FIG. 21).

The movement of the drill shaft 448 is enabled by the flexibility of the material from which the drill shaft 448 is made. Preferably, the drill shaft is made from surgical steel or from any other suitable strong flexible material. The movement may also be assisted by the resiliency of the material from which the gasket 489 is made.

The reciprocating movement of the drill shaft 448 within the slit-like first aperture 487 facilitates the dislodging and freeing of any fragments of the broken cataract which are stuck within the slit-like aperture 487 and prevents clogging and obstructing of the first aperture 487 by such fragments. This dislodging action is further enhanced by the sharp cutting edge 488 which cuts such obstructing fragments reducing their size and facilitating their suction together with the irrigating fluid supplied through the second aperture 478.

It will be appreciated that the first hollow member 486 is narrow at the slit-like first aperture 487 and widens as one moves along the first hollow member 486 in a direction away from the first aperture 487. This feature of the present invention has the advantage of ensuring that most of the fragments of the cataract entering the first aperture 487 will be easily passed through the part of the first hollow member 486 distal of the first aperture 487 and will be removed by suction of the irrigating fluid without clogging the distal part of the first hollow member 486.

It is noted that, in all of the preferred embodiments of the present invention, the irrigation system may be gravity assisted or, alternatively, may be assisted by active pumping means such as a peristaltic pump (not shown) or any other type of suitable pump for pumping the irrigation fluid under pressure. This may be useful since the pumping device may enable even further reduction in the diameter of the tip of the distal shaft of the device since the active pumping may allow the delivery of desirable flow rates of the irrigating fluid from smaller tip diameters.

It is also noted that, while the drilling unit 470 is adapted for use with the handle 262 of FIG. 15 or the handle 290 of FIG. 20, the drilling unit 470 can also be adapted for use with handles such as the handle 220 of FIG. 10A or with any other suitable handle by appropriately modifying the structure of the liquid conduits in a way which is within the spirit of the present invention, It is further noted, that while the cross-sectional area of the slit-like first aperture 487 is shown to be a rectangular aperture having rounded corners, other different types of apertures may also be used such as oval, elliptical or rectangular narrow slit-like apertures and the like.

It is still further noted that, while the drill blade 446 of the drilling unit 470 is illustrated as having a particular shape (FIG. 21), many other different shapes of drill blades may be used as long as they are suitable for drilling into a cataract which is in a solid-like state or frozen or partially frozen.

It will be appreciated that, while the drilling unit 470 includes a second hollow member 484 for forming a fluid conduit to supply irrigation fluid to the anterior chamber of the eye, other preferred embodiments of the invention may be implemented where the irrigation fluid is supplied by the cryomanipulator as disclosed hereinabove, obviating the need for the second hollow member. In such preferred embodiments, a guard lip (not shown) may be attached to the housing It is noted that, while the handles 220, 262 and 290 include spring and ball latches 252, 255 and 308, respectively, any other suitable type of latch can be used.

It is further noted that, while the motor 206 of FIG. 9 is a variable speed electrical motor, any other type of suitable motor can be used to rotate the flexible shaft 214. For example, the motor can be a pneumatic motor operated by a compressed-air supply.

It is yet further noted that, the flexible shaft 214 connected to the CRD 204 and 260 can also be encased within a flexible protective sleeve (not shown) which is detachably connected to the motor 206 at one end and to the handle of the CRD 204 or 260 at the other end.

It is still further noted that, while the vacuum pump 208 of FIG. 9 is controlled by the foot pedal 210, the vacuum pump can also be controlled by any other suitably located controlling device. For example, the vacuum pump 208 can be controlled by a dial placed on the handle of the CRD 204 (not shown). Similarly, the starting, stopping and speed control of the motors 206 and 300 of FIGS. 9 and 20 can be performed using any suitably placed controlling device, such as a suitable foot pedal.

It is additionally noted that the drilling unit 270 of FIG. 15 can also be made in more than one variation, each variation having a different angle between the distal shaft 283 and the handle 262, in the assembled CRD 260 as disclosed in detail for the CRD 204 hereinabove. The surgeon can thus select the most appropriate variation of the drilling unit 270 to be assembled with the handle 262.

It is further noted that the distal shafts 242, 283 and 483 have a length in the range of a few centimeters and a width approximately in the range of a few millimeters across their widest dimension. Preferably these dimensions are optimized to allow the insertion of the distal shafts 242, 283 and 483 into the eye through the smallest possible incision while still having fluid conduits that have a sufficient diameter to allow efficient irrigation and removal by suction of irrigation fluid at the tip of the distal shafts 242, 283 and 483.

It is also noted that the vacuum pump 208 of the system for removing cataract can also include a liquid trap (not shown) for trapping the excess irrigation fluid which is aspired by the CRD 204 and 260 of FIGS. 9 and 15, respectively.

The present invention has been described above in conjunction with the specific application of intraocular surgery, particularly cataract surgery. It should be appreciated, however, that at least some aspects of the present invention may be applicable to other surgical procedures.

While the invention has been described with respect to a limited number of embodiments, it will be appreciated that many variations, modifications and other applications of the invention may be made.

It will be appreciated by persons skilled in the art that the present invention is not limited to what has been thus far described. Rather, the scope of the present invention is limited only by the following claims.

What is claimed is:

1. A device for removing a cataract from an eye, while at least part of the cataract is freeze-gripped in a solid-like state, said device including,
   a drilling unit for breaking the cataract,
   a handle connectable to said drilling unit for enabling an operator to manipulate said drilling unit within the eye,
   said drilling unit additionally comprising:
      a housing including an elongated hollow member having a first portion distal to said handle, and a second portion proximal to said handle,
      said first portion including a first end proximate to said handle and a second end distal to said handle, and an aperture at said second end of said first portion, said aperture constructed and arranged to be a narrow slit-like aperture having a first aperture end and a second aperture end,
      said hollow member adapted for communication with a vacuum pump for aspiring irrigation fluid and fragments of said cataract suspended in said irrigation fluid from the anterior chamber of said eye; and
      a drill bit rotatably disposed within said hollow member, said drill bit adapted for coupling with a motor.

2. The device according to claim 1, wherein said drill bit is movable between said first end and said second end of said aperture to free fragments of said cataract obstructing said aperture.

3. The device according to claim 2, wherein a part of said first portion of said hollow member narrows to form a cutting edge defining said aperture.

4. The device according to claim 1, wherein said drilling unit further comprises:
   a sealing gasket disposed between said hollow member and said drill bit for sealing said first portion of said hollow member to prevent leakage of air through said first portion into said hollow member when said vacuum pump is operating and said second portion of said hollow member is positioned within the anterior chamber of said eye.

5. The device according to claim 4, wherein said sealing gasket is a lubricated gasket.

6. The device according to claim 1, additionally comprising a motor, said motor is disposed within said handle.

7. The device according to claim 1, wherein said second portion of said hollow member has a first substantially uniform cross sectional area, and said first portion of said hollow member progressively narrows towards said aperture.

8. The device according to claim 1, wherein said drill bit includes a drill shaft and a drill blade attached to said drill shaft.

9. The device according to claim 1, wherein said drilling unit is a disposable unit.

10. The device according to claim 1, wherein said drill bit comprises a drill blade and wherein said housing of said drilling unit also comprises a guard lip protruding from an end of said housing proximal to said drill blade and extending along at least part of said drill blade.

11. The device according to claim 1, further comprising at least one controlling unit for controlling said vacuum pump and said motor.

12. The device according to claim 11, wherein said controlling unit also regulates the rate of suction of said vacuum pump and the speed of rotation of said motor.

13. A device for removing a cataract from an eye, while at least part of the cataract is freeze-gripped in a solid-like state, the device including,
   a drilling unit for breaking the cataract,
   a handle connectable to said drilling unit for enabling an operator to manipulate said drilling unit within the eye,
   said drilling unit additionally comprising:
      (a) a housing including a first hollow member and a second hollow member, said first hollow member disposed within said second hollow member and attached thereto, said first hollow member having a first portion distal to said handle, and a second portion proximal to said handle, said first portion including a first end proximate to said handle and a second end distal to said handle;
      (b) a first aperture at said second end of said first portion of said first hollow member, said first aperture constructed and arranged to be a narrow slit-like aperture having a first end and a second end,
      (c) said first hollow member adapted for communication with a vacuum pump for aspiring irrigation fluid and fragments of said cataract suspended in said irrigation fluid from the anterior chamber of said eye,
      (d) said second hollow member including a first end proximate to said handle and a second end distal to said handle, and a second aperture at the second end of said second hollow member, said second hollow member adapted for communication with an irrigation fluid reservoir, for providing irrigation fluid through said second aperture to the anterior chamber of said eye; and
      (e) a drill bit rotatably disposed within said first hollow member, said drill bit adapted for coupling with a motor.

14. The device according to claim 13, wherein said drill bit includes a drill blade and wherein said second hollow member comprises a guard lip protruding from an end of said second hollow member proximal to said drill blade and extending along at least part of said drill blade.

15. The device according to claim 13, wherein said second portion of said first hollow member has a substantially uniform cross sectional area, and said first portion of said first hollow member progressively narrows towards said first aperture.

16. The device according to claim 13, wherein said drill bit includes a drill shaft and a drill blade attached to said drill shaft, said drill shaft is moveable between said first end and said second end of said slit-like first aperture to free fragments of said cataract obstructing said first aperture.

17. The device according to claim 13, wherein drilling unit is a disposable unit.

18. The device according to claim 13, wherein a part of said first portion of said first hollow member narrows to form a cutting edge defining said first aperture.

19. The device according to claim 13, further comprising:
   (a) at least one vacuum pump;
   (b) at least one motor; and
   (c) a controlling unit for controlling said vacuum pump and said motor.

20. The device according to claim 19, wherein said controlling unit also regulates the rate of suction of said vacuum pump and the speed of rotation of said motor.

21. A device for removing a cataract from an eye, while at least part of the cataract is freeze-gripped in a solid-like state, the device including;
   (a) a drilling unit for breaking the cataract,
   (b) a handle connectable to said drilling unit for enabling an operator to manipulate said drilling unit within the eye,
   said drilling unit additionally comprising:
      a housing including a first hollow member and a second hollow member, said first hollow member disposed within said second hollow member and attached thereto;
      said first hollow member having a first portion distal to said handle, and a second portion proximal to said handle;
      said first portion including a first end proximate to said handle and a second end distal to said handle, and a first aperture at said second end, and
      said first portion including a part that narrows to form a cutting edge defining said first aperture;
   said first hollow member adapted for communication with a vacuum pump for aspiring irrigation fluid and fragments of said cataract suspended in said irrigation fluid from the anterior chamber of said eye,
   said second hollow member including a first end proximate to said handle and a second end distal to said handle, and a second aperture at the second end of said second hollow member, said second hollow member adapted for communication with an irrigation fluid reservoir, for providing irrigation fluid through said second aperture to the anterior chamber of said eye; and
   a drill bit rotatably disposed within said first hollow member, said drill bit adapted for coupling with a motor and adapted for moving laterally within said first hollow member.

22. The device according to claim 21, wherein said drill bit includes a drill blade and wherein said second hollow member comprises a guard lip protruding from an end of said second hollow member proximal to said drill blade and extending along at least part of said drill blade.

23. The device according to claim 21, wherein said second portion of said first hollow member has a substantially uniform cross sectional area, and said first portion of said first hollow member progressively narrows towards said first aperture.

24. The device according to claim 21, wherein said first aperture is a narrow slit-like aperture having a first end and a second end.

25. The device according to claim 21, wherein said drill bit includes a drill shaft and a drill blade attached to said drill shaft, said drill shaft is movable between said first end and said second end of said first aperture to free fragments of said cataract obstructing said first aperture.

26. The device according to claim 21, wherein the drilling unit is a disposable unit.

27. The device according to claim 21, further comprising:
   (a) at least one vacuum pump;
   (b) at least one motor; and
   (c) a controlling unit for controlling said vacuum pump and said motor.

28. The device according to claim 27, wherein said controlling unit also regulates the rate of suction of said vacuum pump and the speed of rotation of said motor.

* * * * *